US007179788B2

(12) United States Patent
DeFelippis et al.

(10) Patent No.: US 7,179,788 B2
(45) Date of Patent: Feb. 20, 2007

(54) BIPHASIC MIXTURES OF GLP-1 AND INSULIN

(75) Inventors: Michael Rosario DeFelippis, Carmel, IN (US); Richard Dennis DiMarchi, Carmel, IN (US); Kingman Ng, Carmel, IN (US); Michael Ernst Trautmann, Hamburg (DE)

(73) Assignee: Eli Lilly and Company, Indianapolis, IN (US)

( * ) Notice: Subject to any disclaimer, the term of this patent is extended or adjusted under 35 U.S.C. 154(b) by 206 days.

(21) Appl. No.: 10/490,575

(22) PCT Filed: Oct. 7, 2002

(86) PCT No.: PCT/US02/29842

§ 371 (c)(1),
(2), (4) Date: Mar. 19, 2004

(87) PCT Pub. No.: WO03/035099

PCT Pub. Date: May 1, 2003

(65) Prior Publication Data

US 2004/0254107 A1 Dec. 16, 2004

Related U.S. Application Data

(60) Provisional application No. 60/350,676, filed on Oct. 19, 2001.

(51) Int. Cl.
*A61K 38/26* (2006.01)
*A61K 38/28* (2006.01)

(52) U.S. Cl. .............................. 514/3; 514/12; 530/303; 530/308

(58) Field of Classification Search ..................... None
See application file for complete search history.

(56) References Cited

U.S. PATENT DOCUMENTS

| | | | |
|---|---|---|---|
| 5,118,666 | A | 6/1992 | Habener |
| 5,120,712 | A | 6/1992 | Habener |
| 5,461,031 | A | 10/1995 | De Felippis |
| 5,512,549 | A | 4/1996 | Chen et al. |
| 5,514,646 | A | 5/1996 | Chance et al. |
| 5,545,618 | A | 8/1996 | Buckley et al. |
| 5,547,929 | A | 8/1996 | Anderson, Jr. et al. |
| 5,650,486 | A | 7/1997 | De Felippis |
| 5,656,722 | A | 8/1997 | Dorschug |
| 5,705,483 | A | 1/1998 | Galloway et al. |
| 5,747,642 | A | 5/1998 | De Felippis |
| 5,840,680 | A | 11/1998 | Balschmidt |
| 5,948,751 | A * | 9/1999 | Kimer et al. ............... 514/4 |
| 5,977,071 | A | 11/1999 | Galloway et al. |
| 6,011,007 | A | 1/2000 | Havelund et al. |
| 6,133,235 | A | 10/2000 | Galloway et al. |
| 6,191,102 | B1 | 2/2001 | DiMarchi et al. |
| 6,221,633 | B1 | 4/2001 | Ertl et al. |
| 6,221,837 | B1 | 4/2001 | Ertl et al. |
| 6,268,343 | B1 | 7/2001 | Knudsen et al. |
| 6,277,877 | B1 | 8/2001 | Hoover et al. |
| 2001/0047084 | A1 | 11/2001 | Knudsen et al. |

FOREIGN PATENT DOCUMENTS

| | | |
|---|---|---|
| WO | WO 93/18786 | 9/1993 |
| WO | WO 95/07931 | 3/1995 |
| WO | WO 95/31214 | 11/1995 |
| WO | WO 99/07404 | 2/1999 |
| WO | WO 99/25727 | 5/1999 |
| WO | WO 99/25728 | 5/1999 |
| WO | WO 99/32116 | 7/1999 |
| WO | WO 99/43708 | 9/1999 |
| WO | WO 00/37098 | 6/2000 |
| WO | WO 00/66629 | 11/2000 |
| WO | WO 01/00223 | 1/2001 |
| WO | WO 03/053339 | 7/2003 |

OTHER PUBLICATIONS

DeFelippis et al. 'Preparation and Characterization of a Cocrystalline Suspension of [LYSB28, PROB29]-Human Insulin Analogue', J. of Pharm. Sci. vol. 87, No. 2, Feb. 1998, pp. 170-176.*
Adelhorst, et al., "Structure-Activity Studies of Glucagon-Like Peptide-1." 1994, J. Biological Chemistry vol. 269: 6275-6278.
Brange, "Galenics of Insulin: The Physico-chemical and Pharmaceutical Aspects of Insulin and Insulin Preparation." 1987.
Markussen, et al., "Soluble, Prolonged-acting Insulin Derivatives. III. Degree of Protraction, Crystallizability and Chemical Stability of Insulins Substituted in Positions A21, B13, B23, B27 and B30." Protein Eng. 1988, vol. 2: p. 157-166.
Markussen, et al., "Soluble, Fatty Acid Acylated Insulins Bind to Albumin and Show Protracted Action in Pigs." Diabetologia, 1996, vol. 39, pp. 281-288.
Miki, H. et al., "Glucagon-like Peptide-1(7-36) Amide Enhances Insulin-stimulated Glucose Uptake and Decreases Intracellular cAMP Content in Isolated Rat Adipocytes." Biochimica et Biophysica Acta, 1996, pp. 132-136.
Montrose-Rafizadeh, C., et al., "Pancreatic Glucagon-Like Peptide-1 Receptor Couples to Multiple G Proteins and Activates Mitogen-Activated Protein Kinase Pathways in Chinese Hamster Ovary Cells," Endocrinology, 1999, vol. 140, No. 3, pp. 1132-1140.
Myers, et al., "Acylation of Human Insulin With Palmitic Acid Extends the Time Action of Human Insulin in Diabetic Dogs." Diabetes, 1997, vol. 46, pp. 637-642.
Vella, et al., "Effects of Glucagon-Like Peptide 1 (7-36) Amide on Glucose Effectiveness and Insulin Action in People With Type 2 Diabetes." Diabetes, Apr. 2000, vol. 49, pp. 611-617.
Zander, et al., "Additive Glucose-Lowering Effects of Glucagon-Like Peptide-1 and Metformin in Type 2 Diabetes." Apr. 2001, vol. 24, No. 4, pp. 720-725.
Del Prato, Stefano, et al. "Basal Plasma Insulin Levels Exert a Qualitative But Not Quantitative Effect On Glucose-Mediated Glucose Uptake." The American Physiological Society, pp. E1089-E1095, 1995.

* cited by examiner

*Primary Examiner*—Anish Gupta
(74) *Attorney, Agent, or Firm*—Alejandro Martinez; Gregory A. Cox

(57) ABSTRACT

The present invention encompasses pharmaceutical formulations comprising a biphasic mixture which comprises a glucagon like peptide (GLP-1) compound in a solid phase and an insulin in a solution phase.

6 Claims, No Drawings

SEQUENCE LISTING

```
<160> NUMBER OF SEQ ID NOS: 6

<210> SEQ ID NO 1
<211> LENGTH: 31
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Xaa at position 31 is Gly or absent
<220> FEATURE:
<221> NAME/KEY: MOD_RES
<222> LOCATION: (30)..(30)
<223> OTHER INFORMATION: Arg at position 30 is amidated when Xaa at
      position 31 is absent

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa at position 3 is Asp or Glu
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (2)..(2)
<223> OTHER INFORMATION: Xaa at position 2 is Ser or Gly

<400> SEQUENCE: 2

His Xaa Xaa Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 3
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa at position 1 is desamino-histitide, 2-
      amino-histidine, beta-hydroy-histidine, homohistidine, alpha-
      fluoromethyl-histidine or alpha-methyl-histidine
```

```
-continued

<220> FEATURE:
<221> NAME/KEY: MISC_FEATURE
<222> LOCATION: (1)..(1)
<223> OTHER INFORMATION: Xaa at position 1 is L-histidine, D-histidine,
      or a modified residue
<220> FEATURE:
<221> NAME/KEY: MISC_FEATURE
<222> LOCATION: (3)..(3)
<223> OTHER INFORMATION: Xaa at position 3 is Glu, Asp, Lys, Thr, Ser,
      Arg, Trp, Phe, Tyr, or His
<220> FEATURE:
<221> NAME/KEY: MISC_FEATURE
<222> LOCATION: (2)..(2)
<223> OTHER INFORMATION: Xaa at position 2 is Ala, Gly, Ser, Thr, Leu,
      Ile, Val, Glu, Asp, or Lys
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
      Ile, Val, Glu, Asp, Arg, His, or Lys
<220> FEATURE:
<221> NAME/KEY: MISC_FEATURE
<222> LOCATION: (6)..(6)
<223> OTHER INFORMATION: Xaa at position 6 is His, Trp, Phe, or Tyr
<220> FEATURE:
<221> NAME/KEY: MISC_FEATURE
<222> LOCATION: (8)..(8)
<223> OTHER INFORMATION: Xaa at position 8 is Ser, Ala, Gly, Thr, Leu,
      Ile, Val, Glu, Asp, or Lys
<220> FEATURE:
<221> NAME/KEY: MISC_FEATURE
<222> LOCATION: (10)..(10)
<223> OTHER INFORMATION: Xaa at position 10 is Val, Ala, Gly, Ser, Thr,
      Leu, Ile, Tyr, Glu, Asp, Trp, His, Phe, or Lys
<220> FEATURE:
<221> NAME/KEY: MISC_FEATURE
<222> LOCATION: (11)..(11)
<223> OTHER INFORMATION: Xaa at position 11 is Ser, Ala, Gly, Thr, Leu,
      Ile, Val, Glu, Asp, or Lys
<220> FEATURE:
<221> NAME/KEY: MISC_FEATURE
<222> LOCATION: (12)..(12)
<223> OTHER INFORMATION: Xaa at position 12 is Ser, Ala, Gly, Thr, Leu,
      Ile, Val, Glu, Asp, His, Pro, Arg, or Lys
<220> FEATURE:
<221> NAME/KEY: MISC_FEATURE
<222> LOCATION: (13)..(13)
<223> OTHER INFORMATION: Xaa at position 13 is Tyr, Phe, Trp, Glu, Asp,
      Gly, Gln, Asn, Arg, Cys,, or Lys
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, or Lys
<220> FEATURE:
<221> NAME/KEY: MISC_FEATURE
<222> LOCATION: (15)..(15)
<223> OTHER INFORMATION: Xaa at position 15 is Glu, Asp, or Lys
<220> FEATURE:
<221> NAME/KEY: MISC_FEATURE
<222> LOCATION: (16)..(16)
<223> OTHER INFORMATION: Xaa at position 16 is Gly, Ala, Ser, Thr, Leu,
      Ile, Val, Glu, Asp, or Lys
<220> FEATURE:
<221> NAME/KEY: MISC_FEATURE
<222> LOCATION: (17)..(17)
<223> OTHER INFORMATION: Xaa at position 17 is Gln, Asn, Arg, Glu, Asp,
      His, or Lys
<220> FEATURE:
<221> NAME/KEY: MISC_FEATURE
<222> LOCATION: (19)..(19)
<223> OTHER INFORMATION: Xaa at position 19 is Ala, Gly, Ser, Thr, Leu,
      Ile, Val, Glu, Asp, or Lys
<220> FEATURE:
<221> NAME/KEY: MISC_FEATURE
<222> LOCATION: (20)..(20)
<223> OTHER INFORMATION: Xaa at position 20 is Lys, Arg, Gln, Glu, Asp,
      Trp, Tyr, Phe, or His
```

```
<220> FEATURE:
<221> NAME/KEY: MISC_FEATURE
<222> LOCATION: (21)..(21)
<223> OTHER INFORMATION: Xaa at position 21 is Glu, Asp, Ala, His, Phe,
      Tyr, Trp, Arg, Leu, or Lys
<220> FEATURE:
<221> NAME/KEY: MISC_FEATURE
<222> LOCATION: (24)..(24)
<223> OTHER INFORMATION: Xaa at position 24 is Ala, Gly, Ser, Thr, Leu,
      Ile, Val, Glu, Asp, His, or Lys
<220> FEATURE:
<221> NAME/KEY: MISC_FEATURE
<222> LOCATION: (25)..(25)
<223> OTHER INFORMATION: Xaa at position 25 is Trp, Phe, Tyr, Glu, Asp,
      Ser, Thr, Arg, or Lys
<220> FEATURE:
<221> NAME/KEY: MISC_FEATURE
<222> LOCATION: (26)..(26)
<223> OTHER INFORMATION: Xaa at position 26 is Leu, Gly, Ala, Ser, Thr,
      Ile, Val, Glu, Asp, or Lys
<220> FEATURE:
<221> NAME/KEY: MISC_FEATURE
<222> LOCATION: (29)..(29)
<223> OTHER INFORMATION: Xaa at position 29 is Gly, Ala, Ser, Thr, Leu,
      Ile, Val, Glu, Asp, Arg, Trp, Tyr, Phe, Pro, His, or Lys
<220> FEATURE:
<221> NAME/KEY: MISC_FEATURE
<222> LOCATION: (30)..(30)
<223> OTHER INFORMATION: Xaa at position 30 is Arg, Lys, Glu, Asp, Thr,
      Ser, Trp, Tyr, Phe, Gly, or His
<220> FEATURE:
<221> NAME/KEY: MISC_FEATURE
<222> LOCATION: (31)..(31)
<223> OTHER INFORMATION: Xaa at position 31 is Gly, Ala, Ser, Thr, Leu,
      Ile, Val, Glu, Asp, His, Lys, Arg, Trp, Tyr, Phe, Pro, Pro-NH2, or
      is absent
<220> FEATURE:
<221> NAME/KEY: MISC_FEATURE
<222> LOCATION: (32)..(32)
<223> OTHER INFORMATION: Xaa at position 32 is Arg, Lys, Glu, Asp, Ser,
      His, or is absent
<220> FEATURE:
<221> NAME/KEY: MISC_FEATURE
<222> LOCATION: (33)..(33)
<223> OTHER INFORMATION: Xaa at position 33 is Arg, Lys, Glu, Asp, Ser,
      His, or is absent
<220> FEATURE:
<221> NAME/KEY: MISC_FEATURE
<222> LOCATION: (34)..(34)
<223> OTHER INFORMATION: Xaa at position 34 is Asp, Glu, Gly, Lys, or is
      absent
<220> FEATURE:
<221> NAME/KEY: MISC_FEATURE
<222> LOCATION: (35)..(35)
<223> OTHER INFORMATION: Xaa at position 35 is Phe, Trp, Tyr, Glu, Asp,
      Ala, Lys, or is absent
<220> FEATURE:
<221> NAME/KEY: MISC_FEATURE
<222> LOCATION: (36)..(36)
<223> OTHER INFORMATION: Xaa at position 36 is Ser, Glu, Asp, Pro, Lys,
      or is absent
<220> FEATURE:
<221> NAME/KEY: MISC_FEATURE
<222> LOCATION: (37)..(37)
<223> OTHER INFORMATION: Xaa at position 37 is Ser, Glu, Asp, Pro, Lys,
      or is absent
<220> FEATURE:
<221> NAME/KEY: MISC_FEATURE
<222> LOCATION: (38)..(38)
<223> OTHER INFORMATION: Xaa at position 38 is Gly, Glu, Asp, Pro, Lys,
      or is absent
<220> FEATURE:
<221> NAME/KEY: MISC_FEATURE
<222> LOCATION: (39)..(39)
<223> OTHER INFORMATION: Xaa at position 39 is Ala, Val, Glu, Asp, Ser,
      Lys, Ala-NH2, Val-NH2, Glu-NH2, Asp-NH2, Ser-NH2, Lys-NH2, is
      absent, or is a
      modified residue.
```

```
<220> FEATURE:
<221> NAME/KEY: MOD_RES
<222> LOCATION: (39)..(39)
<223> OTHER INFORMATION: Xaa at position 39 is amidated, a C-1-6-ester,
      a C-1-6-alkyl amide, or a C-1-6-dialkylamide
<220> FEATURE:
<221> NAME/KEY: MISC_FEATURE
<222> LOCATION: (27)..(27)
<223> OTHER INFORMATION: Xaa at position 27 is Val, Gly, Ala, Ser, Thr,
      Leu, Ile, Glu, Asp, Arg, or Lys
<220> FEATURE:
<221> NAME/KEY: MISC_FEATURE
<222> LOCATION: (28)..(28)
<223> OTHER INFORMATION: Xaa at position 28 is Lys, Arg, Glu, Asp, Asn,
      or His
<220> FEATURE:
<221> NAME/KEY: MISC_FEATURE
<222> LOCATION: (18)..(18)
<223> OTHER INFORMATION: Xaa at position 18 is Ala, Gly, Ser, Thr, Leu,
      Ile, Val, Arg, Glu, Asp, or Lys

<400> SEQUENCE: 3

Xaa Xaa Xaa Gly Xaa Xaa Thr Xaa Asp Xaa Xaa Xaa Xaa Xaa Xaa
1               5                   10                  15

Xaa Xaa Xaa Xaa Xaa Phe Ile Xaa Xaa Xaa Xaa Xaa Xaa Xaa Xaa
            20                  25                  30

Xaa Xaa Xaa Xaa Xaa Xaa Xaa
            35

<210> SEQ ID NO 4
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr
<220> FEATURE:
<221> NAME/KEY: MISC_FEATURE
<222> LOCATION: (21)..(21)
<223> OTHER INFORMATION: Xaa at position 21 is Ala, Glu, His, Phe, Tyr,
      Trp, Arg, or Lys
<220> FEATURE:
<221> NAME/KEY: MISC_FEATURE
<222> LOCATION: (24)..(24)
<223> OTHER INFORMATION: Xaa at position 24 is Glu, Asp, Ser, or His
<220> FEATURE:
<221> NAME/KEY: MISC_FEATURE
<222> LOCATION: (16)..(16)
<223> OTHER INFORMATION: Xaa at position 16 is Asp, Glu, Gln, Asn, Lys,
      Arg, Cys, or Cysteic Acid
<220> FEATURE:
<221> NAME/KEY: MISC_FEATURE
<222> LOCATION: (17)..(17)
<223> OTHER INFORMATION: Xaa at position 17 is His, Asp, Lys, Glu, or
      Gln
<220> FEATURE:
<221> NAME/KEY: MISC_FEATURE
<222> LOCATION: (31)..(31)
<223> OTHER INFORMATION: Xaa at position 31 is Lys, Arg, Thr, Ser, Glu,
      Asp, Trp, Tyr, Phe, His, or is absent
<220> FEATURE:
<221> NAME/KEY: MOD_RES
<222> LOCATION: (30)..(30)
<223> OTHER INFORMATION: Arg at position 30 is amidated when Xaa at
      position 31 is absent
```

```
<400> SEQUENCE: 4

His Xaa Glu Gly Thr Phe Thr Ser Asp Val Ser Ser Tyr Leu Glu Xaa
1               5                   10                  15

Xaa Ala Ala Lys Xaa Phe Ile Xaa Trp Leu Val Lys Gly Arg Xaa
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      or is a modified residue
<220> FEATURE:
<221> NAME/KEY: MOD_RES
<222> LOCATION: (1)..(1)
<223> OTHER INFORMATION: Xaa at position 1 is desamino-histitide, 2-
      amino-histidine, beta-hydroy-histidine, homohistidine, alpha-
      fluoromethyl-histidine or alpha-methyl-histidine
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Ser, or Thr
<220> FEATURE:
<221> NAME/KEY: MISC_FEATURE
<222> LOCATION: (6)..(6)
<223> OTHER INFORMATION: Xaa at position 6 is Phe, Trp, or Tyr
<220> FEATURE:
<221> NAME/KEY: MISC_FEATURE
<222> LOCATION: (10)..(10)
<223> OTHER INFORMATION: Xaa at position 10 is Val, Trp, Ile, Leu, Phe,
      or Tyr
<220> FEATURE:
<221> NAME/KEY: MISC_FEATURE
<222> LOCATION: (13)..(13)
<223> OTHER INFORMATION: Xaa at position 13 is Tyr, Trp, or Phe
<220> FEATURE:
<221> NAME/KEY: MISC_FEATURE
<222> LOCATION: (14)..(14)
<223> OTHER INFORMATION: Xaa at position 14 is Leu, Phe, Tyr, or Trp
<220> FEATURE:
<221> NAME/KEY: MISC_FEATURE
<222> LOCATION: (16)..(16)
<223> OTHER INFORMATION: Xaa at position 16 is Gly, Glu, Asp, or Lys
<220> FEATURE:
<221> NAME/KEY: MISC_FEATURE
<222> LOCATION: (19)..(19)
<223> OTHER INFORMATION: Xaa at position 19 is Ala, Val, Ile, or Leu
<220> FEATURE:
<221> NAME/KEY: MISC_FEATURE
<222> LOCATION: (21)..(21)
<223> OTHER INFORMATION: Xaa at position 21 is Glu, Ile, or Ala
<220> FEATURE:
<221> NAME/KEY: MISC_FEATURE
<222> LOCATION: (24)..(24)
<223> OTHER INFORMATION: Xaa at position 24 is Ala or Glu
<220> FEATURE:
<221> NAME/KEY: MISC_FEATURE
<222> LOCATION: (27)..(27)
<223> OTHER INFORMATION: Xaa at position 27 is Val, or Ile
<220> FEATURE:
<221> NAME/KEY: MOD_RES
<222> LOCATION: (30)..(30)
<223> OTHER INFORMATION: Arg at position 30 is amidated or is Arg when
      Xaa at position 31 is absent
<220> FEATURE:
<221> NAME/KEY: MISC_FEATURE
<222> LOCATION: (31)..(31)
<223> OTHER INFORMATION: Xaa at position 31 is Gly, His, or is absent
```

```
<220> FEATURE:
<221> NAME/KEY: MISC_FEATURE
<222> LOCATION: (12)..(12)
<223> OTHER INFORMATION: Xaa at position 12 is Ser, Trp, Tyr, Phe, Lys,
      Ile, Leu, or Val

<400> SEQUENCE: 5

Xaa Xaa Glu Gly Thr Xaa Thr Ser Asp Xaa Ser Xaa Xaa Xaa Glu Xaa
1               5                   10                  15

Gln Ala Xaa Lys Xaa Phe Ile Xaa Trp Leu Xaa Lys Gly Arg Xaa
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa at position 1 is desamino-histitide, 2-
      amino-histidine, beta-hydroy-histidine, homohistidine, alpha-
      fluoromethyl-histidine or alpha-methyl-histidine
<220> FEATURE:
<221> NAME/KEY: MOD_RES
<222> LOCATION: (30)..(30)
<223> OTHER INFORMATION: Arg at position 30 is amidated or is Arg when
      Xaa at position 31 is absent
<220> FEATURE:
<221> NAME/KEY: MISC_FEATURE
<222> LOCATION: (1)..(1)
<223> OTHER INFORMATION: Xaa at position 1 is L-histidine, D-histidine,
      or modified residue
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr
<220> FEATURE:
<221> NAME/KEY: MISC_FEATURE
<222> LOCATION: (10)..(10)
<223> OTHER INFORMATION: Xaa at position 10 is Val, Phe, Tyr, or Trp
<220> FEATURE:
<221> NAME/KEY: MISC_FEATURE
<222> LOCATION: (12)..(12)
<223> OTHER INFORMATION: Xaa at position 12 is Ser, Tyr, Trp, Phe, Lys,
      Ile, Leu, or Val
<220> FEATURE:
<221> NAME/KEY: MISC_FEATURE
<222> LOCATION: (16)..(16)
<223> OTHER INFORMATION: Xaa at position 16 is Gly, Glu, Asp, or Lys
<220> FEATURE:
<221> NAME/KEY: MISC_FEATURE
<222> LOCATION: (19)..(19)
<223> OTHER INFORMATION: Xaa at position 19 is Ala, Val, Ile, or Leu
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (31)..(31)
<223> OTHER INFORMATION: Xaa at position 31 is Gly or is absent

<400> SEQUENCE: 6

Xaa Xaa Glu Gly Thr Phe Thr Ser Asp Xaa Ser Xaa Tyr Leu Glu Xaa
1               5                   10                  15

Gln Ala Xaa Lys Glu Phe Ile Ala Trp Leu Xaa Lys Gly Arg Xaa
            20                  25                  30
```

BIPHASIC MIXTURES OF GLP-1 AND INSULIN

This is the national phase application, under 35 USC 371, for PCT/US02/29842 filed Oct. 7, 2002, which claims the priority of U.S. provisional application No. 60/350,676 filed Oct. 19, 2001.

The present invention relates to biphasic mixtures comprising a glucagon like peptide (GLP-1) solid phase and an insulin solution phase. These biphasic mixtures can be used to treat diseases such as diabetes mellitus.

It has long been the goal of diabetes therapy to administer drugs that result in a pattern of insulin secretion that mimics the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post absorptive phase requiring a sustained delivery of insulin to regulate hepatic glucose output for maintaining optimal fasting blood glucose.

Once oral medications fail to adequately control blood glucose in type 2 diabetics, it becomes extremely important to achieve near normal glycemic control and thereby minimize the complications associated with diabetes. When oral medications fail, the only current alternative is to treat patients with insulin that must be dosed and timed with respect to meal-related glucose excursions and hepatic glucose output during periods of fasting so as to effectively normalize glucose while reducing the risk of hypoglycemia. Control of the absorptive phase involving disposal of the meal-related blood glucose surge can be effectively achieved with commercially available regular insulin and monomeric insulin analogs. However, control of the absorptive phase involving disposal of hepatic glucose output during periods of fasting, especially between meals and during the bedtime hours, is not as effectively achieved with these insulins.

Various commercially available insulin formulations with protracted time actions have been developed to more conveniently treat the post absorptive phase. However, it is often quite difficult for type 2 diabetics to transition from a treatment involving oral medications to one involving injections of insulin that must be carefully administered to avoid complications such as hypoglycemia between meals and during bedtime hours. Thus, there is a need for a more convenient therapy with a reduced risk of hypoglycemia for type 2 diabetics.

Glucagon-like peptide-1 (GLP-1) shows great promise as a treatment for type 2 diabetes especially for those patients no longer able to control blood glucose with oral medications. GLP-1 polypeptides have a variety of physiologically significant activities. For example, GLP-1 has been shown to stimulate insulin release, lower glucagon secretion, inhibit gastric emptying, and enhance glucose utilization. [Nauck, M. A., et al. (1993) *Diabetologia* 36:741–744; Gutniak, M., et al. (1992) *New England J. of Med.* 326:1316–1322; Nauck, M. A., et al., (1993) *J. Clin. Invest.* 91:301–307]. Furthermore, some animal studies suggest that GLP-1 may actually preserve beta cells, inhibit beta cell apoptosis, and induce beta cell proliferation. One of the most exciting observations is that GLP-1 activity is glucose dependent. When levels drop to a certain threshold level, GLP-1 is not active. Thus, there is no risk of hypoglycemia associated with treatment involving GLP-1.

A composition of native GLP-1 and insulin has been suggested by Van Antwerp et al. in WO 01/00223. However, Van Antwerp focuses on thermally stable compositions suitable for continuous infusion using a pump. The usefulness of these compositions by other means of administration is limited because native GLP-1 in solution is cleared extremely fast and has a half-life on the order of five minutes.

Derivatives of GLP-1 analogs have been disclosed in U.S. Pat. No. 6,268,343. These derivatives having a protracted time action, are generally taught as a soluble compostion, which optionally includes an antidiabetic agent, including insulin.

However, it was not understood until the present invention whether an insoluble GLP-1 and an insulin solution could be formulated together such that both agents are chemically and physically stable and retain the desired activities and time actions. The molecular interactions between an insoluble precipitate or crystals of GLP-1 in a suspension and an insulin in solution could compromise the activity and time action of either agent. Furthermore, the conditions necessary to achieve chemical and physical stability are different for each agent when formulated alone.

The present invention focuses on stable biphasic mixtures that provide optimal glycemic control with a reduced risk of hypoglycemia. The biphasic mixtures comprise a GLP-1 solid phase and an insulin solution phase. The GLP-1 solid phase comprises an insoluble GLP-1 precipitate or crystal. The insoluble GLP-1 provides for a slowed absorption rate resulting in GLP-1 with a protracted action that is useful to control disposal of hepatic glucose output during periods of fasting, especially between meals and during the bedtime hours, as well as meal-related blood glucose surges. The insulin solution phase comprises an insulin that can control disposal of the meal-related blood glucose surge, especially after the first meal of the day where glucose levels are potentially the highest.

In one form thereof, the present invention provides a pharmaceutical formulation comprising a biphasic mixture which comprises a glucagon like peptide (GLP-1) compound in a solid phase and an insulin in a solution phase. Preferably GLP-1 compounds have a sequence selected from the group consisting of SEQ ID NO: 1, SEQ ID NO: 2, SEQ ID NO: 3, SEQ ID NO: 4, SEQ ID NO: 5, and SEQ ID NO: 6. Preferably insulins include regular human insulin or a monomeric insulin analog. The monomeric insulin analog is preferably selected from the group consisting of AspB28, AspB28-ProB29, LysB28, LysB28-ProB29, LeuB28, LeuB28-ProB29, ValB28, ValB28-ProB29, AlaB28, AlaB28-ProB29, des B28-30, and des B27. Optionally, the monomeric insulin analog is LysB3-GluB29. The pharmaceutical formulation can optionally comprise an isotonicity agent. The pharmaceutical formulation can optionally comprise a preservative.

The present invention provides a process of preparing biphasic mixtures suitable for use in pharmaceutical formulations by mixing a GLP-1 compound in a solid phase with an insulin in a solution phase, such that the GLP-1 remains in a solid phase and retains the sustained pharmacokinetic profile and the insulin remains in the solution phase and retains a short time action characteristic.

The present invention provides a method of administering the pharmaceutical formulation administering an effective amount of the formulation comprising a biphasic mixture to a patient in need thereof.

The present invention provides a method of treating a medical condition selected from the group consisting of non-insulin dependent diabetes, insulin dependent diabetes, hyperglycemia, obesity, catabolic changes after surgery, myocardial infarction, stress induced hypergycemia, and stroke comprising administering an effective amount of the pharmaceutical formulation comprising a biphasic mixture to a patient in need thereof.

The present invention provides a use of the pharmaceutical formulation comprising a biphasic mixture for the preparation of a medicament in the therapeutic treatment of a medical condition selected from the group consisting of non-insulin dependent diabetes, insulin dependent diabetes, hyperglycemia, obesity, therapeutic reduction of body weight in a human subject, catabolic changes after surgery, myocardial infarction, stress induced hypergycemia, and stroke in a mammal.

The three-letter abbreviation code for amino acids used in this specification conforms with the list contained in Table 3 of Annex C, Appendix 2 of the PCT Administrative Instructions and with 37 C.F.R. § 1.822(d)(1)(2000).

For purposes of the present invention as disclosed and described herein, the following terms and abbreviations are defined as follows.

The term "GLP-1 solid" as used herein refers to one phase of a biphasic mixture. The GLP-1 solid phase comprises an insoluble GLP-1 precipitate or crystal in an aqueous solution, wherein the insoluble GLP-1 precipitate or crystal has a sustained pharmacokinetic profile. The insoluble GLP-1 precipitate or crystal comprises a GLP-1 compound and zinc. Optionally, the insoluble GLP-1 precipitate or crystal further comprises a basic polypeptide.

The term "GLP-1" or GLP-1 compound" as used herein refers to polypeptides that include naturally occurring truncated GLP-1 polypeptides (GLP-1(7-37)OH and GLP-1(7-36)NH$_2$), GLP-1 fragments, GLP-1 analogs, and derivatives thereof. For purposes of the present invention, GLP-1 compounds also include Exendin-3 and Exendin-4, and analogs and derivatives thereof. GLP-1 compounds of the present invention have the ability to bind to the GLP-1 receptor and initiate a signal transduction pathway resulting in insulinotropic activity. Examples of GLP-1 compounds appropriate for use in the present invention are discussed more extensively below.

The term "sustained pharmacokinetic profile" as used herein refers to length of time efficacious levels of biologically active GLP-1 compound is in circulation. It is preferable that the sustained pharamacokinetic profile be such that a single injection adequately controls hepatic glucose output during periods of fasting. It is more preferable that efficacious levels of the GLP-1 compound remain in the serum from about 12 hours to about 24 hours, and most preferably from about 20 hours to about 24 hours.

The term "insulinotropic activity" refers to the ability to stimulate insulin secretion in response to elevated glucose levels, thereby causing glucose uptake by cells and decreased plasma glucose levels. Insulinotropic activity can be assessed by methods known in the art, including using in vivo experiments and in vitro assays that measure GLP-1 receptor binding activity or receptor activation, e.g., assays employing pancreatic islet cells or insulinoma cells, as described in EP 619,322 to Gelfand, et al. (described in Example 1), and U.S. Pat. No. 5,120,712, respectively. Insulinotropic activity is routinely measured in humans by measuring insulin levels or C-peptide levels. For the purposes of the present invention, insulinotropic activity is determined using the method described in Example 1. A GLP-1 compound has insulinotropic activity if islet cells secrete insulin levels in the presence of the GLP-1 compound above background levels. Preferably the biphasic mixtures encompassed by the present invention are comprised of a GLP-1 compound with insulinotropic activity that is equal to or greater than GLP-1(7-37)OH. It is even more preferable that the GLP-1 compound have greater insulinotropic activity than GLP-1(7-37)OH.

The term "insulin solution" as used herein refers to a second phase in a biphasic mixture. The insulin solution phase comprises an aqueous solution comprising a soluble insulin, wherein the insulin has a short time action characteristic. Preferably, the short time characteristic is comparable to commercially available insulins, such as Humulin®, Humalog®, Novolog®, and the like. Insulin includes regular insulins, insulin analogs, or insulin derivatives of regular insulins or insulin analogs that bind to the insulin receptor and initiate the utilization of circulating glucose. It is preferable that the insulin counteract the meal-related blood glucose surge and return glucose levels back to normal physiological range. It is more preferable that insulin counteract the meal-related blood glucose surge and return glucose levels back to normal physiological range within a few hours after a meal. It is more preferable that the insulin counteract the meal-related blood glucose surge and return glucose levels back to normal physiological range within one hour after a meal. It is most preferable that the insulin counteract the meal-related blood glucose surge after the first meal of the day.

Biphasic Mixtures:

The present invention encompasses various biphasic mixtures comprising a GLP-1 compound in a solid phase and an insulin in a solution phase. The final concentrations of the GLP-1 and the insulin in the biphasic mixture will vary depending on the ratios of the two phases. Further, the concentrations will vary depending on the amino acid make-up and potency of the GLP-1 compound and insulin used. The final concentration of the GLP-1 in the biphasic mixture is between about 0.1 mg/mL and about 10 mg/mL. More preferably the final concentration of the GLP-1 is between about 0.1 mg/mL and about 8 mg/mL and more preferably between about 0.1 mg/mL and about 7 mg/mL. Most preferably the final concentration of the GLP-1 is between about 0.1 mg/mL and about 6 mg/mL. The final insulin concentration is less than about 100 U/mL. (For example, 100 U/mL is equal to about 3.5 mg/mL for Humulin® or Humalog®) Preferably the final insulin stock concentration in the biphasic mixture is less than about 75 U/mL. More preferably the final insulin concentration is less than 50 U/mL, and most preferably the final insulin concentration is about 25 U/mL. The skilled artisan will recognize that weights (mg) of commercially available insulins, such as Humulin®, Humalog®, and Novolog® are standardized to the number of units per milliliter.

Pharmaceutical Formulations:

The present invention encompasses pharmaceutical formulations comprising a biphasic mixture suitable for administration to a patient in need thereof. Preferably, the pharmaceutical formulation remains stable for an extended period of time under normal conditions of storage. Preferably, the period of time is more than 6 months at 4° C. or ambient temperature, preferably the period of time is more than 1 year at 4° C. or ambient temperature, more preferably, the period of time is more than 2 years at 4° C. or ambient temperature.

The weight to weight ratio of GLP-1 to insulin is such that after administration of the pharmaceutical formulation, the plasma levels of both the GLP-1 and insulin are maintained within their efficacious ranges. Typically the ratio of GLP-1 to insulin is from about 99:1 (weight:weight) to 10:90 (w/w), more preferably, at a ratio from about 85:15 (w/w) to 15:85

(w/w) (see Example 6). Even more preferably, the ratio of GLP-1 to insulin is from about 85:15 (w/w) to about 50:50 (w/w). Most preferably the ratio of GLP-1 to insulin is about 85:15 (w/w).

Preferably, serum levels of the GLP-1 that has insulinotropic activity within 2-fold that of GLP-1(7-37)OH is maintained between about 30 picomoles/liter and about 200 picomoles/liter for at least a time sufficient to control hepatic glucose output during periods of fasting. Optimum serum levels will be higher for GLP-1 compounds that are less active than GLP-1(7-37)OH or lower for GLP-1 compounds that are more active than GLP-1(7-37)OH. Thus, the concentration of the GLP-1 compound may be adjusted upwards or downwards depending on the activity of the GLP-1 compound in the suspension.

Preferably the serum levels of insulin are such as to counteract the meal-related blood glucose surge and restore plasma glucose levels back to normal, typically blood glucose levels are to about 120–125 mg/dL. Generally, the total insulin daily dose is between about 0.3 U/kg and about 1.5 U/kg. Typically, however, the total mealtime insulin daily dose is between about 50% of the total insulin daily dose, or between about 0.15 U/kg and about 1 U/kg, preferably between about 0.3 U/kg and about 1 U/kg.

The various pharmaceutical formulations of the present invention may optionally encompass a pharmaceutically acceptable buffer. However, the selection, concentration, and pH of the buffer shall be such that the GLP-1 remains in a solid phase and maintains the sustained pharmacokinetic profile and that the insulin remains in the solution phase and maintains the short time action characteristic of counteracting the meal-related blood glucose surge. Examples of pharmaceutically acceptable buffers include phosphate buffers such as dibasic sodium phosphate, TRIS, glycylglycine, maleate, sodium acetate, sodium citrate, sodium tartarate, or an amino acid such as glycine, histidine, lysine or arginine. Other pharmaceutically acceptable buffers are known in the art. Preferably, the buffer is selected from the group consisting of phosphate, TRIS, maleate, and glycine. Even more preferably the buffer is TRIS, glycine, or both.

Preferably, the TRIS concentration is between about 1 mM and 100 mM. Even more preferably, the concentration is between about 10 mM and about 50 mM, most preferably the buffer is about 15 mM. Preferably, the glycine concentration is between about 10 mM to about 50 mM. More preferably, the glycine concentration is between about 20 mM to about 30 mM and more highly preferred is a glycine concentration of between about 23 mM and about 29 mM.

The pH of the pharmaceutical formulations is adjusted to provide acceptable stability, to maintain the sustained pharmacokinetic profile of the GLP-1 solid and the short time action characteristic of the insulin solution, and be acceptable for parenteral administration. Preferably, the pH is adjusted to between about 7.0 and about 8.5, more preferably the pH is between about 7.4 and 8.0, even more preferably the pH is between about 7.4 and 7.8. Most preferably, the pH is about 7.5

The pharmaceutical formulations of the present invention may optionally comprise a preservative. However, the selection and concentration of the preservative shall be such that the GLP-1 remains in a solid phase and maintains sustained pharmacokinetic profile and that the insulin remains in the solution phase and maintains the short time action characteristic. Preservative refers to a compound that is added to a pharmaceutical formulation to act as an anti-microbial agent. A parenteral formulation must meet guidelines for preservative effectiveness to be a commercially viable multi-use product. Among preservatives known in the art as being effective and acceptable in parenteral formulations are phenolic preservatives, alkylparabens, benzyl alcohol, chlorobutanol, resorcinol, and other similar preservatives, and various mixtures thereof. Examples of phenolic derivatives include cresols and phenol or a mixture of cresols and phenol. Examples of cresols include meta-cresol, ortho-cresol, para-cresol, chloro-cresol, or mixtures thereof. Alkylparaben refers to a $C_1$ to $C_4$ alkyl paraben, or mixtures thereof. Examples of alkylparabens include methylparaben, ethylparaben, propylparaben, or butylparaben. The concentrations must be sufficient to maintain preservative effectiveness by retarding microbial growth. Preferably, the preservative is a phenol derivative. More preferably the preservative is a cresol. Even more preferably the preservative is meta-cresol.

A preferred concentration of a preservative in the final mixture is about 1.0 mg/mL to about 20.0 mg/mL. More preferred ranges of concentration of preservative in the final mixture are about 2.0 mg/mL to about 8.0 mg/mL, about 2.5 mg/mL to about 4.5 mg/mL and about 2.0 mg/mL to about 4.0 mg/mL. A most preferred concentration of preservative in the final mixture is about 3.0 mg/mL.

The pharmaceutical formulations of the present invention may optionally comprise an isotonicity agent. However, the selection and concentration of the isotonicity agent shall be such that the GLP-1 remains in a solid phase and maintain sustained pharmacokinetic profile and that the insulin remains in the solution phase and maintains the short time action characteristic. Isotonicity agents refer to compounds that are tolerated physiologically and impart a suitable tonicity to the formulation to prevent the net flow of water across cell membranes. Examples of such compounds include glycerin, salts, e.g., NaCl, and sugars, e.g., dextrose, mannitol, and sucrose. These compounds are commonly used for such purposes at known concentrations. One or more isotonicity agents may be added to adjust the ionic strength or tonicity. The preferred isotonicity agent is NaCl. The concentration of the NaCl is preferably about 110 mM.

A preferred pharmaceutical formulation of the present invention comprises a GLP-1 solid phase and a LysB28-ProB29 insulin solution phase such as Humalog®. Preferably, GLP-1 to LysB28-ProB29 insulin is at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises a GLP-1 solid phase and an AspB28 insulin solution phase such as Novolog®. Preferably, GLP-1 to AspB28 insulin is at a ratio from about at a ratio from about 99:1 (w/w) to 10:90 (w/w) more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises a GLP-1 solid phase and a regular human insulin solution phase such as Humulin®. Preferably, GLP-1 to regular human insulin is at a ratio from about at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises a GLP-1 solid phase and a LysB3-GluB29 insulin solution phase. Preferably, GLP-1 to LysB3-GluB29 insulin is at a ratio from about at a ratio from about 99:1 (w/w) to 10:90 (w/w) more preferably, at a ratio from about 85:15

(w/w) to 15:85 (w/w), and even more preferably at a ratio from about 85:15 (w/w) to about 50:50 (w/w).

In another embodiment, the pharmaceutical formulation comprises a Val$^8$-GLP-1 solid phase and a LysB28-ProB29 insulin solution phase such as Humalog®. Preferably, Val$^8$-GLP-1 to LysB28-ProB29 insulin is at a ratio from about at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises a Val$^8$-GLP-1 solid phase and an AspB28 insulin solution phase such as Novolog®. Preferably, Val$^8$-GLP-1 to AspB28 insulin is at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises a Val$^8$-GLP-1 solid phase and a regular human insulin solution phase such as Humulin®. Preferably, Val$^8$-GLP-1 to regular human insulin is at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises either Exendin-3 solid phase or Exendin-4 solid phase and LysB28-ProB29 insulin solution phase such as Humalog®. Preferably, Exendin-3 or Exendin-4 to LysB28-ProB29 insulin is at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises either Exendin-3 solid phase or Exendin-4 solid phase and an AspB28 insulin solution phase such as Novolog®. Preferably, Exendin-3 or Exendin-4 to AspB28 insulin is at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises either Exendin-3 solid phase or Exendin-4 solid phase and a regular human insulin solution phase such as Humulin®. Preferably, Exendin-3 or Exendin-4 to regular human insulin is at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the pharmaceutical formulation comprises either Exendin-3 solid phase or Exendin-4 solid phase and a LysB3-GluB29 insulin solution phase. Preferably, GLP-1 to LysB3-GluB29 insulin is at a ratio from about at a ratio from about 99:1 (w/w) to 10:90 (w/w) more preferably, at a ratio from about 85:15 (w/w) to 15:85 (w/w), and even more preferably at a ratio from about 85:15 (w/w) to about 50:50 (w/w).

Administration may be via any route known to be effective by the physician of ordinary skill. Preferably, the pharmaceutical formulations of the present invention are administrated parenterally. Parenteral administration includes intramuscular, subcutaneous, intravenous, intraderamal, and intraperitoneal administration routes. Intramuscular and subcutaneous administration routes are more preferred.

Preferably, when injected, the pharmaceutical formulations of the present invention result in a glucose profile that is the same or better than that obtained when the GLP-1 solid in a suspension and insulin solution are administered separately. For example, an injection of the pharmaceutical formulation will result in HbA1$_c$ levels that are the same or lower than the HbA1$_c$ levels observed when the GLP-1 solid in a suspension and insulin solution are administered separately. Also, an injection of the pharmaceutical formulation will preferably mimic the pattern of endogenous insulin secretion in normal individuals. More preferably, when injected, the pharmaceutical formulation will result in a glucose profile that is better than that obtained when the GLP-1 solid in a suspension and insulin solution are administered separately.

The pharmaceutical formulations of the present invention are suitable to treat a disease or condition wherein the physiological effects of administering GLP-1 or insulin improves the disease or condition.

Included are subjects with non-insulin dependent diabetes, insulin dependent diabetes, stroke (see WO 00/16797 by Efendic), myocardial infarction (see WO 98/08531 by Efendic), obesity (see WO 98/19698 by Efendic), catabolic changes after surgery (see U.S. Pat. No. 6,006,753 to Efendic), functional dyspepsia and irritable bowel syndrome (see WO 99/64060 by Efendic). Also included are subjects requiring prophylactic treatment with a basal GLP-1 compound, e.g., subjects at risk for developing non-insulin dependent diabetes (see WO 00/07617). Additional subjects include those with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

The pharmaceutical formulations of the present invention can be used to normalize blood glucose levels, prevent pancreatic β-cell deterioration, induce β-cell proliferation, stimulate insulin gene transcription, up-regulate IDX-1/PDX-1 or other growth factors, improve β-cell function, activate dormant β-cells, differentiate cells into β-cells, stimulate β-cell replication, inhibit β-cell apoptosis, regulate body weight, and induce weight loss.

The pharmaceutical formulations of the present invention preferably have a sustained pharamacokinetic profile that lasts from about 12 hours to about 24 hours, and most preferably have a sustained pharamacokinetic profile that lasts from about 20 hours to about 24 hours. Thus, a method of administering the pharmaceutical formulations of the present invention involves administration of the appropriate dose twice per day before the morning and evening meals, and most preferably once per day before the morning meal.

GLP-1 Compounds:

The GLP-1 compounds of the present invention can be made by a variety of methods known in the art such as solid-phase synthetic chemistry, purification of GLP-1 molecules from natural sources, recombinant DNA technology, or a combination of these methods. For example, methods for preparing GLP-1 peptides are described in U.S. Pat. Nos. 5,118,666, 5,120,712, 5,512,549, 5,977,071, and 6,191,102.

The GLP-1 compounds useful in the present invention include the naturally occurring truncated GLP-1 polypeptides (GLP-1(7-37)OH and GLP-1(7-36)NH$_2$), GLP-1 analogs, Exendin 3, and Exendin-4.

The two naturally occurring truncated GLP-1 peptides are represented in formula I, SEQ ID NO: 1.

```
7   8   9   10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Xaa
``` wherein:

Xaa at position 37 is Gly, or —NH$_2$.

Preferably, a GLP-1 compound has the amino acid sequence of SEQ ID NO: 1 or is modified so that from one, two, three, four or five amino acids differ from SEQ ID NO:1.

Some GLP-1 compounds known in the art include, for example, GLP-1(7-34) and GLP-1(7-35), GLP-1(7-36), Gln$^9$-GLP-1(7-37), D-Gln$^9$-GLP-1(7-37), Thr$^{16}$-Lys$^{18}$-GLP-1(7-37), and Lys$^{18}$-GLP-1(7-37). GLP-1 compounds such as GLP-1(7-34) and GLP-1(7-35) are disclosed in U.S. Pat. No. 5,118,666. Other known biologically active GLP-1 analogs are disclosed in U.S. Pat. Nos. 5,977,071; 5,545,618; 5,705,483; 5,977,071; 6,133,235; Adelhorst, et al., *J. Biol. Chem.* 269:6275 (1994); and Xiao, Q., et al. (2001), *Biochemistry* 40:2860–2869.

GLP-1 compounds also include polypeptides in which one or more amino acids have been added to the N-terminus and/or C-terminus of GLP-1(7-37)OH, or fragments or analogs thereof. Preferably from one to six amino acids are added to the N-terminus and/or from one to eight amino acids are added to the C-terminus of GLP-1(7-37)OH. It is preferred that GLP-1 compounds of this type have up to about thirty-nine amino acids. The amino acids in the "extended" GLP-1 compounds are denoted by the same number as the corresponding amino acid in GLP-1(7-37)OH. For example, the N-terminal amino acid of a GLP-1 compound obtained by adding two amino acids to the N-terminus of GLP-1(7-37)OH is at position 5 and 6; and the C-terminal amino acid of a GLP-1 compound obtained by adding one amino acid to the C-terminus of GLP-1(7-37)OH is at position 38. Amino acids 1–6 of an extended GLP-1 compound are preferably the same as or a conservative substitution of the amino acid at the corresponding position of GLP-1(1-37)OH. Amino acids 38–45 of an extended GLP-1 compound are preferably the same as or a conservative substitution of the amino acid at the corresponding position of Exendin-3 or Exendin-4. The amino acid sequence of Exendin-3 and Exendin-4 are represented in formula II, SEQ ID NO: 2.

```
7   8   9   10  11  12  13  14  15  16  17
His-Xaa-Xaa-Gly-Thr-Phe-Thr-Ser-Asp-Leu-Ser- 18  19  20  21  22  23  24  25  26  27  28
Lys-Gln-Met-Glu-Glu-Glu-Ala-Val-Arg-Leu-Phe- 29  30  31  32  33  34  35  36  37  38  39
Ile-Glu-Trp-Leu-Lys-Asn-Gly-Gly-Pro-Ser-Ser- 40  41  42  43  44  45
Gly-Ala-Pro-Pro-Pro-Ser-NH$_2$
``` wherein:

Xaa at position 8 is Ser or Gly; and

Xaa at position 9 is Asp or Glu.

Exendin-3 has Ser at position 8 and Asp at position 9. Exendin-4 has Gly at position 8 and Glu at position 9. Other GLP-1 compounds of the present invention include formula 2 (SEQ ID NO:2) wherein the C-terminal Ser is the acid form instead of the amidated form. Also, GLP-1 compounds of the present invention include Exendin-3 and Exendin-4 agonists as described in WO99/07404, WO99/25727, WO99/25728, WO99/43708, WO00/66629, and US2001/0047084A1 which are herein incorporated by reference.

A preferred group of GLP-1 compounds are represented in formula III (SEQ ID NO:3):

```
7   8   9   10  11  12  13  14  15  16  17
Xaa-Xaa-Xaa-Gly-Xaa-Xaa-Thr-Xaa-Asp-Xaa-Xaa- 18  19  20  21  22  23  24  25  26  27  28
Xaa-Xaa-Xaa-Xaa-Xaa-Xaa-Xaa-Xaa-Xaa-Xaa-Phe- 29  30  31  32  33  34  35  36  37  38  39
Ile-Xaa-Xaa-Xaa-Xaa-Xaa-Xaa-Xaa-Xaa-Xaa-Xaa- 40  41  42  43  44  45
Xaa-Xaa-Xaa-Xaa-Xaa-Xaa
``` wherein:

Xaa at position 7 is: L-histidine, D-histidine, desamino-histidine, 2-amino-histidine, β-hydroxy-histidine, homohistidine, α-fluoromethyl-histidine or α-methyl-histidine;

Xaa at position 8 is Ala, Gly, Ser, Thr, Leu, Ile, Val, Glu, Asp, or Lys;

Xaa at position 9 is Glu, Asp, Lys, Thr, Ser, Arg, Trp, Phe, Tyr, or His;

Xaa at position 11 is Thr, Ala, Gly, Ser, Leu, Ile, Val, Glu, Asp, Arg, His, or Lys;

Xaa at position 12 is His, Trp, Phe, or Tyr

Xaa at position 14 is Ser, Ala, Gly, Thr, Leu, Ile, Val, Glu, Asp, or Lys;

Xaa at position 16 is Val, Ala, Gly, Ser, Thr, Leu, Ile, Tyr, Glu, Asp, Trp, His, Phe, or Lys;

Xaa at position 17 is Ser, Ala, Gly, Thr, Leu, Ile, Val, Glu, Asp, or Lys;

Xaa at position 18 is Ser, Ala, Gly, Thr, Leu, Ile, Val, Glu, Asp, His, Pro, Arg, or Lys;

Xaa at position 19 is Tyr, Phe, Trp, Glu, Asp, Gly, Gln, Asn, Arg, Cys, or Lys;

Xaa at position 20 is Leu, Ala, Gly, Ser, Thr, Ile, Val, Glu, Asp, Met, or Lys;

-continued

Xaa at position 21 is Glu, Asp, or Lys;

Xaa at position 22 is Gly, Ala, Ser, Thr, Leu, Ile, Val, Glu, Asp, or Lys;

Xaa at position 23 is Gln, Asn, Arg, Glu, Asp, His, or Lys;

Xaa at position 24 is Ala, Gly, Ser, Thr, Leu, Ile, Val, Arg, Glu, Asp, or Lys;

Xaa at position 25 is Ala, Gly, Ser, Thr, Leu, Ile, Val, Glu, Asp, or Lys;

Xaa at position 26 is Lys, Arg, Gln, Glu, Asp, Trp, Tyr, Phe, or His;

Xaa at position 27 is Glu, Asp, Ala, His, Phe, Tyr, Trp, Arg, Leu, or Lys;

Xaa at position 30 is Ala, Gly, Ser, Thr, Leu, Ile, Val, Glu, Asp, His, or Lys;

Xaa at position 31 is Trp, Phe, Tyr, Glu, Asp, Ser, Thr, Arg, or Lys;

Xaa at position 32 is Leu, Gly, Ala, Ser, Thr, Ile, Val, Glu, Asp, or Lys;

Xaa at position 33 is Val, Gly, Ala, Ser, Thr, Leu, Ile, Glu, Asp, Arg, or Lys;

Xaa at position 34 is Lys, Arg, Glu, Asp, Asn, or His;

Xaa at position 35 is Gly, Ala, Ser, Thr, Leu, Ile, Val, Glu, Asp, Arg, Trp, Tyr, Phe, Pro, His, or Lys;

Xaa at position 36 is Arg, Lys, Glu, Asp, Thr, Ser, Trp, Tyr, Phe, Gly, or His;

Xaa at position 37 is Gly, Ala, Ser, Thr, Leu, Ile, Val, Glu, Asp, His, Lys, Arg, Trp, Tyr, Phe, Pro, Pro-NH$_2$ or is deleted;

Xaa at position 38 is Arg, Lys, Glu, Asp, Ser, or His, or is deleted;

Xaa at position 39 is Arg, Lys, Glu, Asp, Ser, or His, or is deleted;

Xaa at position 40 is Asp, Glu, Gly, or Lys, or is deleted;

Xaa at position 41 is Phe, Trp, Tyr, Glu, Asp, Ala, or Lys, or is deleted;

Xaa at position 42 is Ser, Pro, Lys, Glu, or Asp, or is deleted;

Xaa at position 43 is Ser, Glu, Asp, Pro, or Lys, or is deleted;

Xaa at position 44 is Gly, Glu, Asp, Pro, or Lys, or is deleted; and

Xaa at position 45 is Ala, Val, Glu, Asp, Ser, or Lys, or Ala-NH$_2$, Val-NH$_2$, Glu-NH$_2$, Asp-NH$_2$, Ser-NH$_2$, or Lys-NH$_2$, or is deleted, or a C-1-6-ester, or amide, or C-1-6-alkylamide, or C-1-6-dialkylamide thereof; provided that when the amino acid at position 37, 38, 39, 40, 41, 42, 43, or 44 is deleted, then each amino acid downstream of that amino acid is also deleted.

A preferred group of GLP-1 compounds are:

HVEGTFTSDVSSYLEEQAAKEFIAWLVKGRG or G-NH2

HVEGTFTSDVSSYLEEQAAKEFIAWLIDGGPSSGRPPPS or S-NH2

HVEGTFTSDVSSYLEEQAAKEFIAWLVKGRGSSGDPPPS or S-NH2

HVEGTFTSDVSSYLEEQAAKEFIAWLVKGRPSSGDPPPS or S-NH2

HVEGTFTSDVSSYLEEQAAKEFIAWLIKGGPSSGDPPPS or S-NH2

HVEGTFTSDVSSYLEEQAAKEFIAWLIKGGPSSGDPPPS or S-NH2

HVEGTFTSDVSSYLEEQAAKEFIAWLIKGGPSSGDPPPS or S-NH2

HVEGTFTSDVSSYLEEQAAKEFIAWLVKGRPSSGAPPPS or S-NH2

HVEGTFTSDVSSYLEEQAAKEFIAWLVKGRPSSGDPPPS or S-NH2

HVEGTFTSDVSSYLEEQAAKEFIAWLIKGGPSSGAPPPS or S-NH2

HVEGTFTSDVSSYLEEQAVKEFIAWLIKGGPSSGAPPPS or S-NH2

HVEGTFTSDVSSYLEEQAVKEFIAWLVKGGPSSGAPPPS or S-NH2

HVEGTFTSDVSSYLEEQAVKEFIAWLIKGGPSSGDPPPS or S-NH2

HVEGTFTSDVSSYLEEQAAKEFIAWLIKGGGSSGDPPPS or S-NH2

HVEGTFTSDVSSYLEEQAAKEFIAWLIKGPGSSGDPPPS or S-NH2

HVEGTFTSDVSSYLEEQAAKEFIAWLIKGGSPSGDPPPS or S-NH2

HVEGTFTSDVSSYLEEQAAKEFIAWLIKGGPSSGDPPS or S-NH2

HVEGTFTSDVSSYLEEQAAKEFIAWLIKGGPSSGDPPPS or S-NH2

HVEGTFTSDVSSYLEEQAAKEFIAWLIKGGPSSGDAPPS or S-NH2

HVEGTFTSDVSSYLEEQAAKEFIAWLIKGGPSSGDPAPS or S-NH2

HVEGTFTSDVSSYLEEQAAKEFIAWLIKGGPSSGDPPAS or S-NH2

HVEGTFTSDVSSYLEEQAAXEFIAWLIKGGPSSGDAAAS or S-NH2

HVEGTFTSDWSSYLEGQAAKEFIAWLIKGGPSSGAPPPS or S-NH2

```
HVEGTFTSDWSSYLEGQAAKEFIAWLIKGGPSSGAPPPH or H-NH2
HVEGTFTSDVSSYLEGQAAKEFIAWLIKGGPSSGAPPPS or S-NH2
HVEGTFTSDVSSYLEGQAAKEFIAWLIKGGPSSGDPPPS or S-NH2
HVEGTFTSDWSSYLEGQAAKEFIAWLIKGGPSSGAPPPSH or H-NH2
HVEGTFTSDWSSYLEGQAAKEFIAWLIKGGPHSSGAPPPS or S-NH2
HVEGTFTSDVSSYLEGQAAKEFIAWLVKGRGSSGAPPPS or S-NH2
HVEGTFTSDVSSYLEGQAAKEFIAWLVKGGPSSGAPPPS or S-NH2
HVEGTFTSDVSSYLEEQAAKEFIAWLVKGGPSSGAPPPS or S-NH2
HVEGTFTSDVSSYLEEQAAKEFIAWLVKGRGSSGAPPPS or S-NH2
HVEGTFTSDVSSYLEEQAVKEFIAWLIKGRGSSGAPPPS or S-NH2
HVEGTFTSDWSSYLEEQAAKEFIAWLIKGRGSSGAPPPS or S-NH2
HVEGTFTSDVSSYLEEQAAKEFIAWLIKGRGHSSGAPPPS or S-NH2
HVEGTFTSDVSSYLEEQAAKEFIAWLVKGRGHSSGAPPPS or S-NH2
HVEGTFTSDWSSYLEEQAAKEFIAWLIKGGPHSSGAPPPSH or H-NH2
HVEGTFTSDWSSYLEEQAAKEFIAWLIKGGPSSGAPPPSH or H-NH2
HVEGTFTSDVSWYLEGQAVKEFIAWLIKGGPHSSGAPPPS or S-NH2
HVEGTFTSDVSSYLEEQAVKEFIAWLIKGGPSSGAPPPS or S-NH2
HVEGTFTSDVSSYLEEQAVKEFIAWLINKGGPSSGAPPPSH or H-NH2
HVEGTFTSDWSSYLEEQAVKEFIAWLIKGGPHSSGAPPPS or S-NH2
HVEGTFTSDWSSYLEEQAVKEFIAWLIKGGPSSGAPPPSH or H-NH2
HVEGTFTSDWSSYLEEQAVKEFIAWLIKGGPSSGAPPPS or S-NH2
HVEGTFTSDWSKYLEEQAVKEFIAWLIKGGPSSGAPPPSH or H-NH2
HVEGTFTSDVSSYLEEQAVKEFIAWLIKGGPSSGAPPPRG or G-NH2
HVEGTFTSDVSSYLEEQAVKEFIAWLIKGGPSSGAPPPRG or G-NH$_2$
HVEGTFTSDVSSYLEEQAAKEFIAWLVKGGPSSGAPPPS or S-NH$_2$
HVEGTFTSDVSSYLEEQAAKEFIAWLVDGGPSSGRPPPS or S-NH$_2$
HVEGTFTSDVSSYLEEQAAKEFIAWLVDGGPSSGRPPPS or S-NH2
HVEGTFTSDVSSYLEEQAAKEFIAWLVDGGPSSGKPPPS or S-NH2
HVEGTFTSDVSSYLEEQAAKEFIAWLVDGGPSSGRG or G-NH2
HVEGTFTSDVSSYLEEQAAKEFIAWLIKGGPSSGAPPPS or S-NH2
HVEGTFTSDVSSYLEEQAAKEFIAWLVKGGPSWGAPPPS or S-NH2
HVEGTFTSDVSSYLEEQAAKEFIAWLIKGGPSSGAPPPGPS or S-NH2
HVEGTFTSDVSSYLEEQAAKEFIAWLIKGGPSSGAPPPGPSGPS or S-NH2
HVEGTFTSDVSSYLEEQAVKEFIAWLVKGGPSSGAPPPS or S-NH2
```

Another preferred group of GLP-1 compounds is represented in formula IV (SEQ ID NO:4):

```
 7   8   9  10  11  12  13  14  15  16  17
His-Xaa-Glu-Gly-Thr-Phe-Thr-Ser-Asp-Val-Ser- 18  19  20  21  22  23  24  25  26  27  28
Ser-Tyr-Leu-Glu-Xaa-Xaa-Ala-Ala-Lys-Xaa-Phe- 29  30  31  32  33  34  35  36  37
Ile-Xaa-Trp-Leu-Val-Lys-Gly-Arg-R
``` wherein:

Xaa at position 8 is Gly, Ala, Val, Leu, Ile, Ser, or Thr;

Xaa at position 22 is Asp, Glu, Gln, Asn, Lys, Arg, Cys, or Cysteic Acid;

Xaa at position 23 is His, Asp, Lys, Glu, or Gln;

Xaa at position 27 is Ala, Glu, His, Phe, Tyr, Trp, Arg, or Lys;

Xaa at position 30 is Glu, Asp, Ser, or His;

R is: Lys, Arg, Thr, Ser, Glu, Asp, Trp, Tyr, Phe, His, $-NH_2$.

It is also preferable that the GLP-1 compounds of the present invention have other combinations of substituted amino acids. The present invention encompasses a GLP-1 compound comprising the amino acid sequence of formula V (SEQ ID NO:5)

$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-

Glu-$Xaa_{22}$-Gln-Ala-$Xaa_{25}$-Lys-$Xaa_{27}$-Phe-Ile-$Xaa_{30}$-Trp-Leu-$Xaa_{33}$-Lys-

Gly-Arg-$Xaa_{37}$ wherein:

Xaa$_7$ is: L-histidine, D-histidine, desamino-histidine, 2-amino-histidine, β-hydroxy-histidine, homohistidine, α-fluoromethyl-histidine, or α-methyl-histidine;

Xaa$_8$ is: Ala, Gly, Val, Leu, Ile, Ser, or Thr;

Xaa$_{12}$ is: Phe, Trp, or Tyr;

Xaa$_{16}$ is: Val, Trp, Ile, Leu, Phe, or Tyr;

Xaa$_{18}$ is: Ser, Trp, Tyr, Phe, Lys, Ile, Leu, Val;

Xaa$_{19}$ is: Tyr, Trp, or Phe;

Xaa$_{20}$ is: Leu, Phe, Tyr, or Trp;

Xaa$_{22}$ is: Gly, Glu, Asp, Lys;

Xaa$_{25}$ is: Ala, Val, Ile, or Leu;

Xaa$_{27}$ is: Glu, Ile, or Ala;

Xaa$_{30}$ is: Ala or Glu

Xaa$_{33}$ is: Val, or Ile; and

Xaa$_{37}$ is: Gly, His, -NH$_2$, or is absent.

The present invention also encompasses a GLP-1 compound comprising the amino acid sequence of formula VI (SEQ ID NO:6)

Xaa$_7$-Xaa$_8$-Glu-Gly-Thr-Phe-Thr-Ser-Asp-Xaa$_{16}$-Ser-Xaa$_{18}$-Tyr-Leu-Glu-

Xaa$_{22}$-Gln-Ala-Xaa$_{25}$-Lys-Glu-Phe-Ile-Ala-Trp-Leu-Xaa$_{33}$-Lys-Gly-Arg-

Xaa$_{37}$ wherein:

Xaa$_7$ is: L-histidine, D-histidine, desamino-histidine, 2-amino-histidine, β-hydroxy-histidine, homohistidine, α-fluoromethyl-histidine, or α-methyl-histidine;

Xaa$_8$ is:
Gly, Ala, Val, Leu, Ile, Ser, or Thr;

Xaa$_{16}$ is:
Val, Phe, Tyr, or Trp;

Xaa$_{18}$ is:
Ser, Tyr, Trp, Phe, Lys, Ile, Leu, or Val;

Xaa$_{22}$ is:
Gly, Glu, Asp, or Lys;

Xaa$_{25}$ is:
Ala, Val, Ile, or Leu;

Xaa$_{33}$ is:
Val or Ile; and

Xaa$_{37}$ is:
Gly, -NH$_2$, or is absent.

Most preferred GLP-1 compounds comprise GLP-1 analogs wherein the backbone for such analogs or fragments contains an amino acid other than alanine at position 8 (position 8 analogs). Preferred amino acids at position 8 are glycine, valine, leucine, isoleucine, serine, threonine, or methionine and more preferably are valine or glycine.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 22 is glutaric acid, lysine, aspartic acid, or arginine and more preferably glutamic acid or lysine.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 30 is glutamic acid, aspartic acid, serine, or histidine and more preferably glutamic acid.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 37 is histidine, lysine, arginine, threonine, serine, glutamic acid, aspartic acid, tryptophan, tyrosine, phenylalanine and more preferably histidine.

Other preferred GLP-1 compounds are GLP-1 analogs that have the sequence of GLP-1(7-37)OH except that the amino acid at position 8 is preferably glycine, valine, leucine, isoleucine, serine, threonine, or methionine and more preferably valine or glycine and position 22 is glutamic acid, lysine, aspartic acid, or arginine and more preferably glutamic acid or lysine and position 27 is alanine, lysine, arginine, tryptophan, tyrosine, phenylalanine, or histidine and more preferably alanine.

In the nomenclature used herein to describe GLP-1 compounds, the substituting amino acid and its position is indicated prior to the parent structure. For example Val$^8$-GLP-1(7-37)OH designates a GLP-1 compound in which the alanine normally found at position 8 in GLP-1(7-37)OH (formula I, SEQ ID NO:1) is replaced with valine.

Other preferred GLP-1 compounds include: Val$^8$-GLP-1(7-37)OH, Gly$^8$-GLP-1(7-37)OH, Glu$^{22}$-GLP-1(7-37)OH, Asp$^{22}$-GLP-1(7-37)OH, Arg$^{22}$-GLP-1(7-37)OH, Lys$^{22}$-GLP-1(7-37)OH, Cys$^{22}$-GLP-1(7-37)OH, Val$^8$-Glu$^{22}$-GLP-1(7-37)OH, Val$^8$-Asp$^{22}$-GLP-1(7-37)OH, Val$^8$-Arg$^{22}$-GLP-1(7-37)OH, Val$^8$-Lys$^{22}$-GLP-1(7-37)OH, Val$^8$-Cys$^{22}$-GLP-1(7-37)OH, Gly$^8$-Glu$^{22}$-GLP-1(7-37)OH, Gly$^8$-Asp$^{22}$-GLP-1(7-37)OH, Gly$^8$-Arg$^{22}$-GLP-1(7-37)OH, Gly$^8$-Lys$^{22}$-GLP-1(7-37)OH, Gly$^8$-Cya$^{22}$-GLP-1(7-37)OH, Glu$^{22}$-GLP-1(7-36)NH$_2$, Asp$^{22}$-GLP-1(7-36)NH$_2$, Arg$^{22}$-GLP-1(7-36)NH$_2$, Lys$^{22}$-GLP-1(7-36)NH$_2$, Cys$^{22}$-GLP-1(7-36)NH$_2$, Val$^8$-Glu$^{22}$-GLP-1(7-36)NH$_2$, Val$^8$-Asp$^{22}$-GLP-1(7-36)NH$_2$, Val$^8$-Arg$^{22}$-GLP-1(7-36)NH$_2$, Val$^8$-Lys$^{22}$-GLP-1(7-36)NH$_2$, Val$^8$-Cys$^{22}$-GLP-1(7-36)NH$_2$, Gly$^8$-Glu$^{22}$-GLP-1(7-36)NH$_2$, Gly$^8$-Asp$^{22}$-GLP-1(7-36)NH$_2$, Gly$^8$-Arg$^{22}$-GLP-1(7-36)NH$_2$, Gly$^8$-Lys$^{22}$-GLP-1(7-36)NH$_2$, Gly$^8$-Cys$^{22}$-GLP-1(7-36)NH$_2$, Lys$^{23}$-GLP-1(7-37)OH, Val$^8$-Lys$^{23}$-GLP-1(7-37) OH, Gly$^8$-Lys$^{23}$-GLP-1(7-37)OH, His$^{24}$-GLP-1(7-37)OH, Val$^8$-His$^{24}$-GLP-1(7-37)OH, Gly$^8$-His$^{24}$-GLP-1(7-37)OH, Lys$^{24}$-GLP-1(7-37)OH, Val$^8$-Lys$^{24}$-GLP-1(7-37)OH, Gly$^8$-Lys$^{23}$-GLP-1(7-37)OH, Glu$^{30}$-GLP-1(7-37)OH, Val$^8$-Glu$^{30}$-GLP-1(7-37)OH, Gly$^8$-Glu$^{30}$-GLP-1(7-37)OH, Asp$^{30}$-GLP-1(7-37)OH, Val$^8$-Asp$^{30}$-GLP-1(7-37)OH, Gly$^8$-Asp$^{30}$-GLP-1(7-37)OH, Gln$^{30}$-GLP-1(7-37)OH, Val$^8$-Gln$^{30}$-GLP-1(7-37)OH, Gly$^8$-Gln$^{30}$-GLP-1(7-37)OH, Tyr$^{30}$-GLP-1(7-37)OH, Val$^8$-Tyr$^{30}$-GLP-1(7-37)OH, Gly$^8$-Try$^{30}$-GLP-1(7-37)OH, Ser$^{30}$-GLP-1(7-37)OH, Val$^8$-Ser$^{30}$-GLP-1(7-37)OH, Gly$^8$-Ser$^{30}$-GLP-1(7-37)OH, His$^{30}$-GLP-1(7-37)OH, Val$^8$-His$^{30}$-GLP-1(7-37)OH, Gly$^8$-His$^{30}$-GLP-1(7-37)OH, Glu$^{34}$-GLP-1(7-37)OH, Val$^8$-Glu$^{34}$-GLP-1(7-37)OH, Gly$^8$-Glu$^{34}$-GLP-1(7-37)OH, Ala$^{34}$-GLP-1(7-37)OH, Val$^8$-Ala$^{34}$-GLP-1(7-37)OH, Gly$^8$-Ala$^{34}$-GLP-1(7-37)OH, Gly$^{34}$-GLP-1(7-37)OH, Val$^8$-Gly$^{34}$-GLP-1(7-37)OH, Gly$^8$-Gly$^{34}$-GLP-1(7-37)OH, Ala$^{35}$-GLP-1(7-37)OH, Val$^8$-Ala$^{35}$-GLP-1(7-37)OH, Gly$^8$-Ala$^{35}$-GLP-1(7-37)OH, Lys$^{35}$-GLP-1(7-37)OH, Val$^8$-Lys$^{35}$-GLP-1(7-37)OH, Gly$^8$-Lys$^{35}$-GLP-1(7-37)OH, His$^{35}$-GLP-1(7-37)OH, Val$^8$-His$^{35}$-GLP-1(7-37)OH, Gly$^8$-His$^{35}$-GLP-1(7-37)OH, Pro$^{35}$-GLP-1(7-37)OH, Val$^8$-Pro$^{35}$-GLP-1(7-37)OH, Gly$^8$-Pro$^{35}$-GLP-1(7-37)OH, Glu$^{35}$-GLP-1 (7-37)OH Val$^8$-Glu$^{35}$-GLP-1(7-37)OH, Gly$^8$-Glu$^{35}$-GLP -1(7-37)OH, Val$^8$-Ala$^{27}$-GLP-1(7-37)OH, Val$^8$-His$^{37}$-GLP-1(7-37)OH, Val$^8$-Glu$^{22}$Lys$^{23}$-GLP-1(7-37)OH, Val$^8$-Glu$^{22}$-Glu$^{23}$-GLP-1(7-37)OH, Val$^8$-Glu$^{22}$-Ala$^{27}$-GLP-1(7-37)OH, Val$^8$-Gly$^{34}$-Lys$^{35}$-GLP-1(7-37)OH, Val$^8$-His$^{37}$-GLP-1(7-37)OH, and Gly$^8$-His$^{37}$-GLP-1(7-37)OH.

More preferred GLP-1 compounds are Val$^8$-GLP-1(7-37)OH, Gly$^8$-GLP-1(7-37)OH, Glu$^{22}$-GLP-1(7-37)OH, Lys$^{22}$-GLP-1(7-37)OH, Val$^8$-Glu$^{22}$-GLP-1(7-37)OH, Val$^8$-Lys$^{22}$-GLP-1(7-37)OH, Gly$^8$-Glu$^{22}$-GLP-1(7-37)OH, Gly$^8$-Lys$^{22}$-GLP-1(7-37)OH, Glu$^{22}$-GLP-1(7-36)NH$_2$, Lys$^{22}$-GLP-1(7-36)NH$_2$, Val$^8$-Glu$^{22}$-GLP-1(7-36)NH$_2$, Val$^8$-Lys$^{22}$-GLP-1(7-36)NH$_2$, Gly$^8$-Glu$^{22}$-GLP-1(7-36) NH$_2$, Gly$^8$-Lys$^{22}$-GLP-1(7-36)NH$_2$, Val$^8$-His$^{37}$-GLP-1(7-37)OH, Gly$^8$-His$^{37}$-GLP-1(7-37)OH, Arg$^{34}$-GLP-1(7-36)NH$_2$, and Arg$^{34}$-GLP-1(7-37)OH.

Other preferred GLP-1 compounds include: Val$^8$-Tyr$^{12}$-GLP-1(7-37)OH, Val$^8$-Tyr$^{12}$-GLP-1(7-36)NH$_2$, Val$^8$-Trp$^{12}$-GLP-1(7-37)OH, Val$^8$-Leu$^{16}$-GLP-1(7-37)OH, Val$^8$-Tyr$^{16}$-GLP-1(7-37)OH, Gly$^8$-Glu$^{22}$-GLP-1(7-37)OH, Val$^8$-Leu$^{25}$-GLP-1(7-37)OH, Val$^8$-Glu$^{30}$-GLP-1(7-37)OH, Val$^8$-His$^{37}$-GLP-1(7-37)OH, Val$^8$-Tyr$^{12}$-Tyr$^{16}$-GLP-1(7-37)OH, Val$^8$-Trp$^{12}$-Glu$^{22}$-GLP-1 (7-37)OH, Val$^8$-Tyr$^{12}$-Glu$^{22}$-GLP-1(7-37)OH, Val$^8$-Tyr$^{16}$-Phe$^{19}$-GLP-1(7-37)OH, Val$^8$-Tyr$^{16}$-Glu$^{22}$-GLP-1(7-37)OH, Val$^8$-Trp$^{16}$-Glu$^{22}$-GLP-1(7-37)OH, Val$^8$-Leu$^{16}$-Glu$^{22}$-GLP-1 (7-37)OH, Val$^8$-Ile$^{16}$Glu$^{22}$-GLP-1 (7-37)OH, Val$^8$-Phe$^{16}$-Glu$^{22}$-GLP-1(7-37)OH, Val$^8$-Trp$^{18}$-Glu$^{22}$-GLP-1(7-37)OH, Val$^8$-Tyr$^{18}$-Glu$^{22}$-GLP-1(7-37)OH, Val$^8$-Phe$^{19}$-Glu$^{22\text{-}GLP}$-1(7-37)OH, Val$^8$-Ile$^{18}$Glu$^{22}$-GLP-1(7-37)OH, Val$^8$-Lys$^{18}$-Glu$^{22}$-GLP-1(7-37)OH, Val$^8$-Trp$^{19}$-Glu$^{22}$-GLP-1(7-37)OH, Val$^8$-Phe$^{19}$-Glu$^{22}$-GLP-1 (7-37) OH, Val$^8$-Phe$^{20}$-Glu$^{22}$-GLP-1(7-37)OH, Val$^8$-Glu$^{22}$-Leu$^{25}$-GLP-1(7-37)OH, Val$^5$-Glu$^{22}$-Ile$^{25}$-GLP-1(7-37)OH, Val$^8$-Glu$^{22}$-Val$^{25}$-GLP-1(7-37)OH, Val$^8$-Glu$^{22}$-Ile$^{27}$-GLP-1(7-37)OH, Val$^8$-Glu$^{22}$-Ala$^{27}$-GLP-1(7-37)OH, Val$^8$-Glu$^{22}$-Ile$^{33}$-GLP-1(7-37)OH, Val$^8$-Glu$^{22}$-His$^{37}$-GLP-1(7-37)OH, Val$^8$-Asp$^{19}$-Ile$^{11}$-Tyr$^{16}$-Glu$^{22}$-GLP-1(7-37)OH, Val$^8$-Tyr$^{16}$-Trp$^{19}$-Glu$^{22}$-GLP-1 (7-37)OH, Val$^8$-Trp$^{16}$-Glu $^{22}$-Val$^{25}$Ile$^{33}$-GLP-1(7-37)OH, Val$^8$-Trp$^{16}$-Glu$^{22}$-Ile$^{33}$-GLP-1(7-37)OH, Val$^8$-Glu$^{22}$-Val $^{22}$-Val$^{25}$Ile$^{33}$-GLP-37)OH, and Val$^8$-Trp$^{16}$-Glu$^{22}$-Val$^{25}$-GLP-1(7-37)OH.

Zinc Crystals:

A GLP-1 compound can be incorporated into zinc crystals. Preferably, an alkaline normalization step is performed. The pH of the GLP-1 solution is adjusted to between about 9.5 and about 11.5. This step appears to reduce the content of β-sheet conformation in the peptide and enhance the α-helix conformation that is important for solubility and bioavailability of some GLP-1 compounds. This step also serves to maintain the peptide in a preferred α-helix conformation prior to the subsequent process step. This key step thus "normalizes" variation in bulk lots of the peptide into a more reproducible, homogenous solution.

Preferably, the peptide concentration in the alkaline normalization solution is greater than 5 mg/mL. More preferably, the concentration is about 10 mg/mL to about 30 mg/mL. Other ranges of preferred concentration of dissolved peptide are about 5 mg/mL to about 25 mg/mL, about 8 mg/mL to about 25 mg/mL and about 10 mg/mL to about 20 mg/mL. The most preferred concentration is about 15 mg/mL.

Preferably, an aqueous alkaline solution comprising only water and a base such as NaOH, KOH or ammonium hydroxide is employed to dissolve the peptide. A more preferred base is NaOH.

Preferably, the pH of the alkaline normalization step is about 10.0 to about 11.0. More preferably, the pH is about 10.5. The alkaline solution comprising the dissolved peptide may be allowed to sit quiescently for a period of about 5 minutes to about 3 hours at ambient temperature, which, although it is not to be construed as a limitation, is generally between about 20° C. and about 25° C. The alkaline solution may also be gently stirred. More preferably, the dissolved alkaline peptide solution will sit quiescently for about 1 hour at ambient temperature. One skilled in the art will recognize that combinations of pH, time, temperature and stirring conditions for this step can be readily established for each peptide that ensures "normalization" of the peptide conformation is complete yet avoids or minimizes chemical degradation that may occur to the peptide.

The next step in the process for preparing crystals of a selected peptide is the addition of glycine. Amino acids such as glycine bind zinc ions which also bind very tightly to the histidine residue(s) in a peptide. Thus, competition for zinc binding may play a role in the formation of peptide crystals, as well as in the stability of subsequent crystalline compositions. The glycine added to the alkaline peptide solution may be in a solid form or in a stock solution. Preferably, glycine is added as a solid. Preferably, the added glycine is in free-base form. Preferably, the resulting concentration of glycine in the alkaline peptide solution is about 5 mM to about 250 mM. Ranges of more preferred glycine concentration are about 10 mM to about 150 mM, about 20 mM to about 100 mM, about 40 mM to about 80 mM and about 55 mM to about 65 mM. Most preferably, the glycine concentration is about 60 mM.

Optionally, the pH of the alkaline peptide solution may be readjusted after the addition of the glycine. If the pH is adjusted, it is preferably adjusted to a pH between about 9.0 and about 11.0. More preferably, it is adjusted to a pH between about 9.2 and about 9.8. Most preferably, it is adjusted to about pH 9.5.

Optionally, the alkaline peptide solution with added glycine may be filtered. Filtration is recommended if any evidence of undissolved particles, dust or lint is apparent in the solution. If desired, this is also a good place in the process at which the solution can be sterilized by performing an aseptic filtration step. Preferably, the filtration will be conducted using a sterile non-pyrogenic filter having low-protein binding and a pore size of 0.45 μm or less. Preferably, the filter is a sterile non-pyrogenic, low-protein binding filter of pore size 0.22 μm or less. More preferably, the filter is a sterile 0.22 μm Millex® filter (Millipore Corporation, Waltham, Mass., USA).

The next step in the process of forming crystals is addition to the alkaline peptide solution of about 2% to about 20% of the total final volume of an alcohol selected from the group consisting of ethanol and isopropanol, and about 0.5 moles to about 2.5 moles of zinc per mole of the peptide. The zinc and ethanol may be added in a single aqueous stock solution or may be added separately in one or more steps in any order. Preferably, the alcohol is added before the zinc is added.

Preferably, the added alcohol represents, by volume, about 2% to about 20% of the total final volume of the alkaline peptide-zinc-alcohol solution. More preferably, the alcohol represents about 5% to about 15% of the total final volume. More preferably, the alcohol represents about 6% to about 12% of the total final volume. Most preferably, the alcohol represents about 9% of the total final volume. Preferably, the alcohol is ethanol.

The zinc added at this stage refers to the zinc ion. The zinc may be added in a variety of forms, but a zinc oxide solution acidified with dilute HCl and salt forms such as zinc acetate or zinc chloride are preferred. More preferred is a zinc oxide solution acidified with dilute HCl.

Preferably, 1.0 moles to about 2.25 moles of zinc per mole of the peptide is added in this process step. Other preferred ranges of zinc addition include 1.1 to 2.0 moles of zinc per mole of the peptide, 1.3 to 1.7 moles per mole of peptide, and 1.4 to 1.6 moles per mole of peptide. Most preferably, about 1.5 moles of zinc per mole of peptide is added.

Preferably, the solution comprising zinc that is added to the peptide solution is added slowly and/or in small increments, which minimizes the localized precipitation of peptide and/or zinc complexes that may form at the site of addition. More preferably, glycine is also a component of the solution comprising zinc that is being added at this step. For example, a zinc-glycine solution may be prepared by dissolving zinc oxide in dilute HCl to a pH of about 1.6 and then adding solid glycine. A sufficient quantity of glycine is added to raise the pH of the solution to between about pH 2 and about pH 3. The pH of the zinc-glycine solution may be raised further using, for example, dilute NaOH. A preferred pH range of the zinc-glycine solution is about pH 4.0 to about pH 6.0. A more preferred pH range of the zinc-glycine solution is about pH 5.0 to about pH 5.5. As noted earlier, glycine has a binding affinity for zinc that may compete with zinc binding to the peptide. Thus, the presence of glycine in the solution comprising zinc that is being added to the composition allows the zinc solution to be added more quickly because localized precipitation problems are minimized. In addition, having a zinc-glycine solution above pH 2.0, and preferably about pH 4.0 to about pH 6.0, allows the solution to be sterile filtered using filters that are rated by their manufacturers to handle, for example, pH 2–10 solutions, prior to its introduction into a sterile peptide composition. Preferably, the zinc-glycine solution comprises about 50 mM to about 70 mM glycine and about 20 mM to about 200 mM zinc.

The last steps in the initial crystallization of a selected peptide are adjusting the pH of the solution to between about pH 7.5 and about pH 10.5 and allowing crystals of the peptide to form. Preferred reagent solutions useful for adjusting the pH of the solution include dilute HCl, dilute acetic acid and dilute NaOH.

Preferred pH ranges for crystallization of selected peptides include about pH 8.0 to about pH 10.0, about pH 7.5 to about pH 9.5, about pH 8.5 to about pH 9.2, about pH 9.0 to about pH 9.5, about pH 7.5 to about pH 8.5, about pH 8.7 to about pH 9.5, and about pH 9.2 to about pH 10.0.

One skilled in the art will recognize that the preferred pH of crystallization will depend on many factors, including the nature of the peptide and its concentration, the alcohol concentration, the zinc concentration, the ionic strength of the solution and the temperature of crystallization. By way of illustration, the peptide Val$^8$-Glu$^{30}$-GLP-1(7-37)OH produced crystals at only select ethanol and zinc concentrations at a pH range of about 7.7 to about 8.1, whereas the peptide Val$^8$-His$^{37}$-GLP-1(7-37)OH produced crystals over a broad range of zinc and ethanol concentrations at a pH range of about 9.8 to about 10.4.

The skilled artisan will further recognize that, for a given set of conditions, a preferred manner of determining the optimal pH of crystallization is to determine it empirically, that is, to slowly add the acidification solution, preferably dilute HCl or dilute acetic acid, in small increments, and observe what happens after each increment is added. Generally, small quantities of localized zones of precipitation will occur at the spot of addition of the acidic solution. When gentle swirling takes increasingly longer periods of time to completely redissolve the precipitation, that is the best time to stop adding the acid and allow crystallization from the clear or slightly cloudy solution to proceed.

The skilled artisan will further recognize that the pH and temperature that one selects for crystallization will have an impact on the speed at which the crystallization proceeds, the crystallization yield, and the size and homogeneity of the crystals formed. Preferably, the pH of crystallization for the selected peptides is about pH 8.0 to about pH 10. More preferably, the pH is about 8.7 to about 9.5. Other ranges of preferred pH of crystallization are about 8.8 to about 9.3, about 9.0 to about 9.5, and about 8.5 to about 9.3. Most preferably, the crystallization is conducted at about pH 9.1.

Preferably, the temperature of crystallization is about 10° C. to about 30° C. More preferably, the temperature of crystallization is about 15° C. to about 28° C. Most preferably, the temperature of crystallization is ambient temperature, or about 20° C. to about 25° C.

Preferably, the crystallization step described above is complete, that is, 90% or more of the peptide is precipitated in predominantly crystalline form, in about 3 hours to about 72 hours. More preferably, the crystallization is complete in about 10 hours to about 48 hours. Most preferably, the crystallization is complete in about 16 hours to about 26 hours. Completion of crystallization may be determined by a variety of means, including HPLC analysis of the peptide present in an aliquot of the composition. Method 5 herein describes one such protocol that may be employed. Preferably, the crystals produced according to the steps of the process described above are thin plate crystals. The crystals produced by the process may be examined by microscopy.

The pH of the suspension of crystals in the original mother liquor is lowered to a pH value at which 97% or more of the peptide becomes insoluble. Preferably, this part of the process begins within a few hours after the initial crystallization is determined to be complete. Preferably, the pH is lowered using a dilute solution of HCl or acetic acid wherein the acidic solution is added slowly and in incremental portions. The skilled artisan will recognize that the preferred pH at which this second stage of crystallization should occur will depend on many factors, including the nature of the peptide and its concentration, the alcohol concentration, the zinc concentration, the ionic strength of the suspension and the temperature of crystallization. Preferably, the pH is about 0.2 to 2.0 pH units lower than the pH at which initial crystallization proceeded. More preferably, the pH is about 0.5 to about 1.5 pH units lower, and most preferably, the pH is about 0.8 to 1.3 pH units lower than the pH at which the initial crystallization proceeded. The temperature of this second stage of crystallization is preferably ambient temperature, or about 20° C. to about 25° C. For the peptide Val$^8$-GLP-1(7-37)OH, a preferred pH is about 7.5 to about 8.5. A more preferred pH is about 7.8 to about 8.2.

Preferably, the pH of a suspension of peptide crystals is lowered to a pH at which 98% or more, and more preferably at which 99% or more of the peptide becomes insoluble in the composition. The additional precipitation formed in this second stage of crystallization comprises crystals. Preferably, the additional precipitation formed in this second stage of crystallization will be predominantly crystals of comparable morphology and size distribution as those formed in the first stage of crystallization.

Preferably, the second stage of crystallization is complete enough, that is, 97% or more of the peptide is insoluble, to allow the following step to begin within 30 hours, more preferably within 18 hours, more preferably within 6 hours and most preferably within 2 hours of when the second stage of crystallization started. Quantitation of precipitation yield may be determined by a variety of means, including HPLC analysis of the peptide present in an aliquot of the suspension.

The steps as described above will result in a stock suspension comprising an insoluble GLP-1 precipitate or crystals in the original mother liquor from the initial crystallization stage. The stock suspension can be mixed with an insulin solution in its present form or the stock suspension may optionally include other suitable, pharmaceutically acceptable excipients.

Optionally, the stock GLP-1 suspension may include a pharmaceutically acceptable buffer such as TRIS, maleate, phosphate, succinate, glycylglycine or adipate, and one or more tonicity agents such as sodium chloride, other salts, glycerin or mannitol. These components may be added as a single solution, as combination solutions or individually in any order. Of these components, a preferred buffer is selected from the group consisting of TRIS, maleate and glycylglycine, and a preferred tonicity agent is sodium chloride. A more preferred buffer is TRIS.

A preferred quantity of TRIS to add to the stock GLP-1 suspension, if TRIS is the selected buffer, is such that the TRIS concentration in the final composition is about 5 mM to about 40 mM. A more preferred range of TRIS concentration in the final composition is about 10 mM to about 20 mM. A most preferred concentration of TRIS in the final composition is about 15 mM.

A preferred quantity of maleate to add to the stock GLP-1 suspension, if maleate is the selected buffer, is such that the maleate concentration in the final composition is about 2 mM to about 20 mM. A more preferred range of maleate concentration in the final composition is about 5 mM to about 15 mM. A most preferred concentration of maleate in the final composition is about 9 mM.

If sodium chloride is selected to be a component of the stock GLP-1 suspension peptide composition, a preferred quantity to add is such that the added sodium chloride in the stock suspension is about 30 mM to about 200 mM. A more preferred concentration of added sodium chloride in the stock suspension is 50 mM to about 150 mM. Other ranges of preferred sodium chloride concentration are about 80 mM to about 120 mM, about 70 mM to about 130 mM, and about 90 mM to about 130 mM. A most preferred quantity of added sodium chloride in the stock suspension is about 110 mM.

Although any pharmaceutically acceptable preservative may be added to the stock GLP-1 suspension at this point in the process, a phenolic preservative or benzyl alcohol is preferred. Examples of phenolic preservatives include phenol, chlorocresol, m-cresol, o-cresol, p-cresol, ethylparaben, methylparaben, propylparaben, butylparaben, thymol or mixtures thereof. More preferred preservatives are benzyl alcohol, m-cresol, phenol, methylparaben and mixtures thereof. A most preferred pharmaceutically acceptable preservative is m-cresol.

The final step in the process of preparing a stock GLP-1 suspension is an adjustment to a final pH between about 6.0 and about 8.5, and preferably between about pH 6.5 and about pH 8.0, and more preferably between about pH 7.0 and about pH 8.0. Although any of a wide variety of acidification and/or alkalization reagent solutions may be employed for this pH adjustment, dilute HCl, dilute NaOH and dilute acetic acid are preferred. More preferred reagent solutions are dilute HCl and dilute NaOH. The preferred pH to which the composition is adjusted will depend to some extent upon the selected peptide, the peptide concentration, the proposed route of administration and the selected buffer.

Preferably, with TRIS as the selected buffer, the pH will be adjusted to a pH between about 6.5 and about 8.5. More preferably, the pH will be adjusted to a pH between about 7.0 and about 7.8, between about 7.2 and about 7.8, between about 7.5 and about 8.5, or between about 7.0 and about 8.0. A most preferred pH to which the stock GLP-1 suspension is adjusted when TRIS is the selected buffer is about 7.5. With maleate as the selected buffer, the pH will be adjusted to a pH between about 6.0 and about 7.5. More preferably, the pH will be adjusted to a pH between about 6.4 and about 7.5, between about 6.4 and about 7.0, or between about 6.0 and about 7.0. A most preferred pH to which the stock GLP-1 suspension is adjusted when maleate is the selected buffer is about 6.5.

Protamine Complexes:

In another embodiment, the GLP-1 solid phase can be a complex comprising a GLP-1 compound and a basic polypeptide. Optionally, the complex comprises a divalent metal ion such as zinc. The complex can be either crystalline or amorphous material or a mixture of crystalline and amorphous material. A crystalline complex is comprised primarily of individual or clusters of microcrystals, rods, needles, or plates or mixtures thereof. An amorphous complex comprises a precipitate, but lacks matter in a crystalline state and a definable form or structure. Basic polypeptides include but are not limited to basic proteins or polyamines. Examples of basic proteins or polyamines are polylysine, polyarginine, polyornithine, protamine, putrescine, spermine, spermidine, and histone. Preferred basic polypeptides are polyarginine, protamine, polylysine, and polyornithine. More preferred is polylysine, polyarginine, and protamine. Most preferred is protamine. Protamine is the generic name of a group of strongly basic proteins present in sperm cell nuclei in salt like combination with nucleic acids. Commercially available protamines can be isolated from mature fish sperm and are usually obtained as the sulfate. The peptide composition of a specific protamine may vary depending on which family, genera or species of fish it is obtained from. Protamine from salmon or trout can be separated into two, three, or more main fractions of proteins that may be separated further. The different parent peptides consist of about 30 amino acids of which more than 20 are arginines. The average molecular weight of protamine is about 4,300. Commercially available protamine sulfate is approximately 80% protamine.

The complex may be prepared by mixing a GLP-1. compound solution with a basic polypeptide solution. A GLP-1 compound solution is preferably a buffered solution and is prepared by dissolving GLP-1 compound in a selected buffer. Examples of a buffer include but are not limited to TRIS, Glycine, Arginine, and Phosphate. A preferred buffer is TRIS. The concentration of buffer should be such that changes in hydrogen ion concentration that would otherwise occur as a result of chemical reactions are minimized. The pH of the GLP-1 solution is about $pH^6$ to about pH 10, preferably about pH 7 to about pH 10, more preferably about pH 8 to about pH 10, and most preferably about pH 9 to about pH 10. The pH of the GLP-1 compound solution can be adjusted based on the isoelectric point (pI) of the GLP-1 compound being dissolved to optimize the amount of GLP-1 compound that will dissolve and remain soluble in the buffered GLP-1 solution. For example, it is preferable that $Val^8$-GLP-1(7-37)OH be dissolved in a TRIS buffered solution wherein the pH is adjusted to 9.0.

The basic polypeptide solution is preferably a buffered solution prepared by dissolving a basic polypeptide in a selected buffer. Examples of a buffer include but are not limited to TRIS, Glycine, Arginine, and Phosphate. A preferred buffer is TRIS. The concentration of buffer should be such that changes in hydrogen ion concentration that would otherwise occur as a result of chemical reactions are minimized. The pH of the buffered basic polypeptide solution is about pH 6 to about pH 10, preferably about pH 7 to about pH 10, more preferably about pH 8 to about pH 10, and most preferably about pH 9 to about pH 10. The concentration of basic polypeptide in solution is about 1.0 to about 20.0 mg/mL. However, ultimately, the concentration of basic polypeptide will be such that when the basic polypeptide solution is added to the GLP-1 compound solution the desired ratio of GLP-1 compound to basic polypeptide is achieved. For example, it is preferable that protamine is dissolved in a Tris buffered solution at a pH of 9.0.

To induce complex formation and reduce adhesion of the complex to reaction vessels, an alcohol selected from the group consisting of ethanol, propanol, isopropanol, and methanol, or mixtures thereof, is added to either the buffered GLP-1 compound solution, the buffered basic polypeptide solution, or both solutions. It is preferred that the final concentration of alcohol once the buffered GLP-1 compound solution and the buffered basic polypeptide solution are mixed is between about 0.2 and about 10% (volume to volume) (v/v). Most preferred is an ethanol concentration between about 4% and 5% (v/v).

The complex is prepared by mixing a buffered GLP-1 compound solution with a buffered basic polypeptide solution. A suspension of amorphous precipitate is initially formed. However, if primarily crystalline complexes are desired, the suspension is incubated for about 18 to 24 hours. Although the temperature of incubation is not critical, it is preferable that the temperature be between about 5° C. and about 35° C. to avoid denaturation of the peptide and to preserve the crystalline matrix that forms. Preferably, the temperature is about 25° C. The amount of time and temperature of incubation can be varied depending on whether amorphous complexes, crystalline complexes, or a mixture of amorphous and crystalline complexes are desired.

The amount of the GLP-1 solution and the basic peptide solution to be mixed together may be adjusted depending on the concentration of GLP-1 compound and basic polypeptide and alcohol in each solution such that the ratios of GLP-1 compound to basic polypeptide in the final mixture range from about 4:1 to about 10:1 (w/w). The final ratio of GLP-1 compound to basic polypeptide affects the morphology as well as the ultimate yield of the complex. For example, a ratio that generally results in crystalline complexes comprised of individual and clusters of microcrystals, rods, needles, plates or mixtures thereof is about 5:1 (w/w) (GLP-1 compound:basic polypeptide), whereas a ratio of 4:1 (w/w) (GLP-1 compound:basic polypeptide) additionally results in larger clusters of microcrystals, rods, needles, and plates.

The yield of complex formation at ratios between about 4:1 and about 5:1 (w/w of GLP-1 compound to basic polypeptide) is generally near 100%. However, the ratio of GLP-1 compound to basic polypeptide can be increased to above 5:1 (GLP-1 compound: basic polypeptide) even though this results in a decreased yield. The concentrations of GLP-1 compound in the GLP-1 solution and basic polypeptide in the basic polypeptide solution can be adjusted such that the ratios of GLP-1 compound to basic polypeptide range from about 6:1 to about 10:1 (w/w), and more preferably from about 7:1 to about 9:1 (w/w)(GLP-1 compounds:basic polypeptide). The yield of complex formation at these ratios is less than 95%, usually less than 90%.

In another embodiment, a divalent metal ion such as zinc is added to the suspension of GLP-1/protamine complex to improve the yield and change the solubility properties of complexes. The solubility characteristics of the complex can be effected depending on the amount of zinc added relative to the amount of GLP-1 compound present. Such a method for controlling the solubility characteristics is useful because the solubility characteristics of the complex determine the drug release rate at the site of delivery. Hence by controlling the solubility characteristics, one can control the pharmacokinetic properties of the drug. Furthermore, soaking the suspension in a solution of zinc can drive the complex formation to completion.

Zinc is preferably added as a salt. Representative examples of zinc salts include zinc acetate, zinc bromide, zinc chloride, zinc fluoride, zinc iodide and zinc sulfate. The skilled artisan will recognize that there are many other zinc salts that also might be used. Preferably, zinc oxide, zinc acetate or zinc chloride is used. A buffered zinc solution at pH of between about 5 and about 6 can be added to the suspension of GLP-1 compound/basic polypeptide complex. A preferred buffer for the buffered zinc solution is glycine. Optionally, an acidic zinc solution at pH of between about 1 and about 2 can be added to the suspension. The preferred final molar ratio of zinc to GLP-1 compound is less than about 2:1. Although the temperature of incubation is not critical, the suspension is generally incubated in the presence of zinc between about 18 and about 24 hours at a temperature between about 5° C. and about 25° C.

Insulins:

Insulin peptides can be made by a variety of methods well known in the art such as solid-phase synthetic chemistry, purification of insulin from natural sources, recombinant DNA technology, or a combination of these methods.

Examples of insulin peptides of the present invention include regular human insulin and monomeric insulin analogs. Examples of preferred monomeric insulin analogs are human insulin wherein proline at position 28 of the Beta chain is substituted with aspartic acid, lysine, leucine, valine, or alanine and lysine at position 29 of the Beta chain is lysine or proline (AspB28 or AspB28-ProB29, LysB28 or LysB28-ProB29, LeuB28 or LeuB28-ProB29, ValB28 or ValB28-ProB29, AlaB28 or AlaB28-ProB29); deletion of amino acids 28, 29 and 30 of the Beta chain (des B28-30);

or deletion of amino acid 27 of the Beta chain (des B27). More preferred monomeric insulin analogs are LysB28-ProB29 and AspB28. Preparations of various monomeric insulin analogs are disclosed in U.S. Pat. Nos. 5,474,978, and 700,662, and are herein incorporated by reference.

Other examples of monomeric insulin analogs include derivatives or physiologically tolerable salts thereof in which asparagine (Asn) in position B3 of the B chain is replaced by a naturally occurring basic amino acid residue and at least one amino acid residue in the positions B27, B28 or B29 of the B chain is replaced by another naturally occurring amino acid residue, it optionally being possible for asparagine (Asn) in position 21 of the A chain to be replaced by Asp, Gly, Ser, Thr or Ala and for phenylalanine (Phe) in position B1 of the B chain and the amino acid residue in position B30 of the B chain to be absent. Preferably B3 is His, Arg, or Lys. Preferrably B27, B28, or B29 is Ile, Asp, or Glu. A preferred monomeric insulin analog of this genus is LysB3-GluB29. Preparations of this genus of monomeric insulin analogs are disclosed in U.S. Pat. No. 6,221,633 and is herein incorporated by reference.

Process of Preparing Biphasic Mixtures

The present invention further provides a process of preparing biphasic mixtures suitable for use in pharmaceutical formulations by mixing a GLP-1 solid with an insulin solution. Insoluble GLP-1 precipitates or crystals may be added as a solid to a solution containing an insulin, or solid soluble insulin may be dissolved in a suspension containing insoluble GLP-1 precipitates and crystals. Alternatively, both the insoluble GLP-1 precipitates or crystals and the soluble insulin may be added in any order to a buffered solution. It is preferred that stock GLP-1 suspensions and stock insulin solutions be prepared separately and then added together at the desired ratio. Preferably, a GLP-1 suspension is diluted with an insulin solution. The GLP-1 suspension and the insulin solution must be mixed in such a way that the GLP-1 remains in a solid phase and maintains the sustained pharmacokinetic profile and that the insulin remains in the solution phase and maintains the short time action characteristic.

Preferably, the process comprises mixing a GLP-1 suspension with a LysB28-ProB29 insulin solution of example 5 at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the process comprises mixing a GLP-1 suspension with an AspB28 insulin solution at a ratio from about 99:1 (w/w) to 10:90 (w/w) more preferably, at a ratio from about 85:15 (w/w) to 15:85 (w/w), and even more preferably at a ratio from about 85:15 (w/w) to about 50:50 (w/w).

In another embodiment, the process comprises mixing a GLP-1 suspension with a regular human insulin solution at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the process comprises mixing $Val^8$-GLP-1 suspension of example 3 with a LysB28-ProB29 insulin solution of example 5 at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the process comprises mixing $Val^8$-GLP-1 suspension of example 3 with an AspB28 insulin solution at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the process comprises mixing $Val^8$-GLP-1 suspension of example 3 with a regular human insulin solution at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the process comprises mixing either Exendin-3 suspension or Exendin-4 suspension with a LysB28-ProB29 insulin solution of example 5 at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the process comprises mixing either Exendin-3 suspension or Exendin-4 suspension with an AspB28 insulin solution at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

In another embodiment, the process comprises mixing either Exendin-3 suspension or Exendin-4 suspension with a regular human insulin solution at a ratio from about 99:1 (w/w) to 10:90 (w/w), more preferably, at a ratio from about 85:15 (w/w) to 15:85 (w/w), and even more preferably at a ratio from about 85:15 (w/w) to about 50:50 (w/w).

The process can optionally comprise the additional step of adding a buffer to the GLP-1 suspension, the insulin solution, or the biphasic mixture of GLP-1 and insulin. Preferably the buffer is TRIS, glycine, or both.

The process can optionally comprise the additional step of adding a preservative to the GLP-1 suspension, the insulin solution, or the biphasic mixture of GLP-1 and insulin.

The process can optionally comprise the additional step of adding an isotonicity agent to the GLP-1 suspension, the insulin solution, or the biphasic mixture of GLP-1 and insulin.

The process can optionally comprise the additional step of adding a preservative to the GLP-1 suspension, the insulin solution, or the biphasic mixture of GLP-1 and insulin.

The invention is illustrated by the following examples which are not intended to be limiting in any way.

EXAMPLE 1

Insulinotropic Activity Determination

A collagenase digest of pancreatic tissue is separated on a Ficoll gradient (27%, 23%, 20.5%, and 11% in Hank's balanced salt solution, pH 7.4). The islets are collected from the 20.5%/11% interface, washed and handpicked free of exocrine and other tissue under a stereomicroscope. The islets are incubated overnight in RPMI 1640 medium supplemented with 10% fetal bovine plasma and containing 11 mM glucose at 37° C. and 95% air/5% $CO_2$. The GLP-1 compound to be studied is prepared at a range of concentrations, preferably 3 nanomolar to 30 nanomolar in RPMI medium containing 10% fetal bovine plasma and 16.7 mM glucose. About 8 to 10 isolated islets are then transferred by pipette to a total volume of 250 μl of the GLP-1 compound containing medium in 96 well microtiter dishes. The islets are incubated in the presence of the GLP-1 compound at 37° C., 95% air, 5% $CO_2$ for 90 minutes. Then aliquots of islet-free medium are collected and 100 μl thereof are

EXAMPLE 2

Zinc Crystallization of Val[8]-GLP-1(7-37)OH

Val[8]-GLP-1(7-37)OH was dissolved in about 15 mL of sterile water for injection at a concentration of about 20 mg/mL. The pH was adjusted to about 10.8 with NaOH and held at ambient temperature for about 30 minutes. To this peptide solution was added 66.8 mg glycine and the pH was adjusted to about 9.5 with NaOH.

The solution was then pressure filtered through a 0.22 μm Millex®-GV (Millipore Corporation, Waltham, Mass., USA) sterilizing filter membrane unit.

To the stirred, sterile filtrate was added 3.3 mL of a sterile 50%(by volume) ethanol solution that had been prepared from absolute ethanol and water for injection.

To this stirred solution was added 0.89 mL of a sterile-filtered buffered zinc oxide solution that had been prepared by combining about 1.221 mg zinc oxide, about 12 mL of 10% Hydrochloric acid, about 85 mL water for injection, and 528.7 mg glycine. The pH of the zinc oxide solution was adjusted to 5.68 with about 3 to 4 mL of 10% NaOH and the final volume was adjusted to 100 mL with water for injection.

The pH of the resulting Val[8]-GLP-1 solution was adjusted to about 9.1 with NaOH. After gently mixing for about 5 minutes, the crystallization solution was covered tightly and held quiescently at ambient temperature for crystallization. At this point the Val[8]-GLP-1 concentration was determined to be about 12.9 mg/mL, glycine concentration was about 50 mM, ethanol concentration was about 9% and zinc oxide concentration was 7 mM (0.46 mg/mL).

After about 24 hours the crystallization process was complete. Analyses typically showed mostly thin, plate-like crystals in a yield greater than 98%.

EXAMPLE 3

Preparing the Stock Val[8]-GLP-1 Suspension.

To 15 mL of the completed crystallization suspension described in Example 2 was added, with stirring, 15 mL of a sterile-filtered solution comprising about 30 mM TRIS, 220 mM NaCl, and 6 mg/mL m-cresol at about pH 7.5.

The stable suspension prepared as described above comprised about 6.5 mg/mL of thin, plate-like crystals of Val[8]-GLP-1(7-37)OH, about 24.8 mM glycine, about 3 mg/mL m-cresol, about 110 mM sodium chloride, about 4.3% ethanol by volume, about 0.23 mg/mL zinc, about 15 mM TRIS and has a pH of about 7.5.

EXAMPLE 4

Preparation of Insulin

LysB28-ProB29 insulin was dissolved in about 15 mL of 0.01N HCl at a concentration of about 200 U/mL. To this solution, 68 mg of glycine was added and the pH was adjusted to 7.5 with NaOH. The resulting solution was pressure filtered through a 0.22 μm Millex®-GV (Millipore Corporation, Waltham, Mass., USA) sterilizing filter membrane unit.

assayed for the amount of insulin present by radioimmunoassay using an Equate Insulin RIA Kit (Binax, Inc., Portland, Me.).

EXAMPLE 5

Preparing the Stock LysB28-ProB29 Insulin Solution.

To 15 mL of the LysB28-ProB29 insulin solution described in Example 4 was added, with stirring, 15 mL of a sterile-filtered solution comprising about 30 mM TRIS, 220 mM NaCl, and 6 mg/mL m-cresol at about pH 7.5.

The stable pharmaceutical solution prepared as described above comprised about 100 U/mL of LysB28-ProB29 insulin, about 30 mM glycine, about 3 mg/mL m-cresol, about 110 mM sodium chloride, about 15 mM TRIS and has a pH of about 7.5.

EXAMPLE 6

Val[8]-GLP-1 Suspension/LysB28-ProB29 Insulin Solution Mixtures

The Val[8]-GLP-1 suspension of example 3 was mixed with the LysB28-ProB29 insulin solution of example 5 at two different ratios.

Mixuture A (85:15, GLP-1:insulin, weight:weight) was prepared by mixing 15 mL of stock Val[8]-GLP-1 suspension with 5 mL of stock LysB28-ProB29 insulin solution. The resulting mixture comprised about 4.9 mg/mL (1.4 mM) Val[8]-GLP-1, about 25 U/mL LysB28-ProB29 insulin, about 26 mM glycine, about 0.17 mg/mL zinc, about 15 mM TRIS, about 110 mM sodium chloride, about 3.2% ethanol by volume, about 3 mg/mL m-cresol, and has a pH of about 7.5.

Mixuture B (38:62, GLP-1:insulin, weight:weight) was prepared by mixing 5 mL of stock Val[8]-GLP-1 suspension with 15 mL of stock LysB28-ProB29 insulin solution. The resulting mixture comprised about 1.6 mg/mL (0.48 mM) Val[8]-GLP-1, about 75 U/mL LysB28-ProB29 insulin, about 29 mM glycine, about 0.06 mg/mL zinc, about 15 mM TRIS, about 110 mM sodium chloride, about 1.1% ethanol by volume, about 3 mg/mL m-cresol, and has a pH of about 7.5.

EXAMPLE 7

Stability Studies of the Mixtures

The mixtures described in example 6 were tested for stability at two and four weeks at 5° C. and 30° C. The volume diameter distribution was determined using a laser light scattering particle analyzer such as Coulter LS 230. (Coulter Electronics Limited, Luton, Beds, England). The samples were also analyzed by reversed-phase HPLC chromatography to determine the total protein concentrations and the soluble protein concentrations. The data are summarized below.

Mixture A at 5° C.

Size measured by Coulter:

|  | V mean (μm) | 10% < (μm) | 50% < (μm) | 90% < (μm) |
|---|---|---|---|---|
| Initial | 7.61 | 1.84 | 7.15 | 14.1 |
| 2 weeks | 7.50 | 1.89 | 6.98 | 13.8 |
| 4 weeks | 7.33 | 1.77 | 6.84 | 13.5 |

Val[8]-GLP-1 HPLC analysis:

|  | Total potency (mg/mL) | Immediately Available (mg/mL) | Supernatant (mg/mL) |
|---|---|---|---|
| Initial | 5.14 | 0.012 | 0.003 |
| 2 weeks | 4.69 | 0.020 | 0.014 |
| 4 weeks | 5.02 | 0.020 | 0.022 |

LysB28-ProB29 Insulin HPLC Analysis:

|  | Total potency (mg/mL) | Immediately Available (mg/mL) | Supernatant (mg/mL) |
|---|---|---|---|
| Initial | 0.98 | 0.95 | 0.85 |
| 2 weeks | 0.90 | 0.96 | 0.87 |
| 4 weeks | 0.92 | 0.84 | 0.88 |

Mixture A at 30° C.

Size Measured by Coulter:

|  | V mean (μm) | 10% < (μm) | 50% < (μm) | 90% < (μm) |
|---|---|---|---|---|
| Initial | 7.61 | 1.84 | 7.15 | 14.1 |
| 2 weeks | 8.02 | 1.96 | 7.53 | 14.7 |
| 4 weeks | 7.25 | 1.72 | 6.82 | 13.4 |

Val[8]-GLP-1 HPLC Analysis:

|  | Total potency (mg/mL) | Immediately Available (mg/mL) | Supernatant (mg/mL) |
|---|---|---|---|
| Initial | 5.14 | 0.012 | 0.003 |
| 2 weeks | 4.95 | 0.016 | 0.130 |
| 4 weeks | 5.40 | 0.015 | 0.034 |

LysB28-ProB29 Insulin HPLC Analysis:

|  | Total potency (mg/mL) | Immediately Available (mg/mL) | Supernatant (mg/mL) |
|---|---|---|---|
| Initial | 0.98 | 0.95 | 0.85 |
| 2 weeks | 0.94 | 0.97 | 0.90 |
| 4 weeks | 0.86 | 0.86 | 0.94 |

Mixture B at 5° C.

Size measured by Coulter:

|  | V mean (μm) | 10% < (μm) | 50% < (μm) | 90% < (μm) |
|---|---|---|---|---|
| Initial | 7.61 | 1.84 | 7.15 | 14.1 |
| 2 weeks | 7.50 | 1.82 | 7.07 | 13.8 |
| 4 weeks | 7.72 | 1.75 | 6.98 | 13.6 |

Val[8]-GLP-1 HPLC Analysis:

|  | Total potency (mg/mL) | Immediately Available (mg/mL) | Supernatant (mg/mL) |
|---|---|---|---|
| Initial | 1.71 | 0.014 | 0.002 |
| 2 weeks | 1.82 | 0.020 | 0.043 |
| 4 weeks | 1.66 | 0.018 | 0.019 |

LysB28-ProB29 Insulin HPLC Analysis:

|  | Total potency (mg/mL) | Immediately Available (mg/mL) | Supernatant (mg/mL) |
|---|---|---|---|
| Initial | 2.59 | 2.60 | 2.52 |
| 2 weeks | 2.63 | 2.72 | 2.60 |
| 4 weeks | 2.56 | 2.46 | 2.65 |

Mixture B at 30° C.

Size measured by Coulter:

|  | V mean (μm) | 10% < (μm) | 50% < (μm) | 90% < (μm) |
|---|---|---|---|---|
| Initial | 7.61 | 1.84 | 7.15 | 14.1 |
| 2 weeks | 8.10 | 1.94 | 7.70 | 14.8 |
| 4 weeks | 7.29 | 1.70 | 6.85 | 13.4 |

Val[8]-GLP-1 HPLC Analysis:

|  | Total potency (mg/mL) | Immediately Available (mg/mL) | Supernatant (mg/mL) |
|---|---|---|---|
| Initial | 1.71 | 0.014 | 0.002 |
| 2 weeks | 1.98 | 0.019 | 0.180 |
| 4 weeks | 1.88 | 0.015 | 0.017 |

LysB28-ProB29 Insulin HPLC Analysis:

|  | Total potency (mg/mL) | Immediately Available (mg/mL) | Supernatant (mg/mL) |
|---|---|---|---|
| Initial | 2.59 | 2.60 | 2.52 |
| 2 weeks | 2.78 | 2.86 | 2.74 |
| 4 weeks | 2.59 | 2.75 | 2.78 |

EXAMPLE 8

In Vivo Studies

Val[8]-GLP-1 Suspension/LysB28-ProB29 Insulin Solution Mixtures are Prepared as Described in Example 6.

The mixture is injected into a single site such that 0.74 U/kg LysB28-ProB29 insulin (1.5 nmol/kg Val[8]-GLP-1 suspension) is administered. A 3-hour hyperglycemic (150 mg/dl) clamp is initiated and glucose infusion rates are continually recorded. Blood samples are taken periodically for the determination of plasma glucose, insulin, C-peptide, and immunoreactive GLP-1 concentrations. Plasma glucose concentrations are determined on the day of study. The remainder of the samples are then frozen (−80° C.) and assayed for hormone concentration determinations at a later time.

---

We claim:

1. A pharmaceutical formulation comprising a biphasic mixture which comprises a GLP-1 compound in a solid phase and an insulin in a solution phase.

2. The pharmaceutical formulation of claim 1 wherein the GLP-1 compound has a sequence selected from the group consisting of SEQ ID NO: 1, SEQ ID NO: 2, SEQ ID NO: 3, SEQ ID NO: 4, SEQ ID NO: 5, and SEQ ID NO: 6.

3. The pharmaceutical formulation of claim 1 wherein the insulin is selected from the group consisting of; AspB28, AspB28-ProB29, LysB28, LysB28-ProB29, LysB3-GluB29, LeuB28, LeuB28-ProB29, ValB28, ValB28-ProB29, AlaB28, AlaB28-ProB29, des(B28-B30)-human insulin; and des (B27)-human insulin.

4. The pharmaceutical formulation of claim 3 wherein the insulin is AspB28.

5. The pharmaceutical formulation of claim 3 wherein the insulin is LysB28-ProB29.

6. The pharmaceutical formulation of claim 1 wherein the GLP-1 compound has a sequence of SEQ ID NO: 2 or SEQ ID NO: 3 and the insulin is AspB28, LysB28-ProB29, or LysB3-GluB29.

* * * * *